(12) United States Patent
Terhune et al.

(10) Patent No.: US 9,205,116 B2
(45) Date of Patent: *Dec. 8, 2015

(54) BACILLUS BACTERIA FOR USE IN TREATING AND PREVENTING INFECTION IN AQUATIC ANIMALS

(75) Inventors: Jeffery Terhune, Auburn, AL (US); Mark Liles, Auburn, AL (US); Joseph Kloepper, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/460,238

(22) Filed: Apr. 30, 2012

(65) Prior Publication Data

US 2012/0328572 A1  Dec. 27, 2012

Related U.S. Application Data

(60) Provisional application No. 61/480,622, filed on Apr. 29, 2011.

(51) Int. Cl.

| A61K 35/742 | (2015.01) |
| A23K 1/18 | (2006.01) |
| A23K 1/00 | (2006.01) |
| A61K 35/76 | (2015.01) |
| A61K 31/165 | (2006.01) |
| A61K 31/505 | (2006.01) |
| A61K 31/635 | (2006.01) |
| A61K 35/74 | (2015.01) |

(52) U.S. Cl.
CPC ............... *A61K 35/742* (2013.01); *A23K 1/004* (2013.01); *A23K 1/009* (2013.01); *A23K 1/188* (2013.01); *A61K 31/165* (2013.01); *A61K 31/505* (2013.01); *A61K 31/635* (2013.01); *A61K 35/74* (2013.01); *A61K 35/76* (2013.01)

(58) Field of Classification Search
None
See application file for complete search history.

(56) References Cited

U.S. PATENT DOCUMENTS

| 6,422,174 B1 | 7/2002 | Horikawa et al. |
| 6,524,998 B1 | 2/2003 | Kloepper et al. |
| 8,445,255 B2 * | 5/2013 | Kloepper et al. .......... 435/252.5 |
| 2008/0226682 A1 * | 9/2008 | Brake et al. ................ 424/278.1 |
| 2010/0092431 A1 | 4/2010 | Liles et al. |
| 2012/0149571 A1 * | 6/2012 | Kloepper et al. ............. 504/117 |

FOREIGN PATENT DOCUMENTS

| CN | 1780557 | 5/2006 |
| CN | 102191189 | 9/2011 |
| CN | 103060222 | 4/2013 |
| EP | 0287699 | 7/1993 |
| WO | 03047353 | 6/2003 |
| WO | 2004044186 | 5/2004 |
| WO | 2004050832 | 6/2004 |
| WO | 2004095939 | 11/2004 |
| WO | 2008041786 | 4/2008 |
| WO | WO 2008/041786 A1 * | 4/2008 |
| WO | 2012079073 | 6/2012 |
| WO | 2012089782 | 7/2012 |

OTHER PUBLICATIONS

Aly et al. Aquaculture 277: 1-6, 2008.*
Tan et al. Lett. Appl. Microbiol. 53: 509-517, 2011.*
Virk et al. Bioresour. Technol. 86: 25-27, 2003, abstract.*
Abrams et al., "Effect of the normal microbial flora on the resistance of the small intestine to infection", Journal of Bacteriology, 1966, 92: 1604-1608.
Birnboim et al., "A rapid alkaline extraction procedure for screening recombinant plasmid DNA", 1979, Nucleic Acids Research, 1979, 7: 1513-1523.
Depaola et al., "Oxytetracycline-medicated feed on antibiotic resistance of gram-negative bacteria in Catfish Ponds", Applied and Environmental Microbiology, 1995, 61: 2335-2340.
Desilva et al., "Estimation of nitrogen and phosphorus in effluent from the striped catfish farming sector in the Mekong Delta, Vietnam", Ambio, 2010, 39: 504-514.
Ford et al., "S-layer positive motile aeromonads isolated from channel catfish", Journal of Wildlife Diseases, 1991, 27: 557-561.
Harlander, "The Evolution of Modern Agriculture and Its Future with Biotechnology", Journal of the American College of Nutrition, 2002, 21: 161S-165S.
Jack et al., Characterization of the chemical and antimicrobial properties of piscicolin 126, a bacteriocin produced by Carnobacterium piscicola JG126, 1996, 62: 2897-2903.
Kloepper et al., "Induced systemic resistance and promotion of plant growth by *Bacillus* spp.", Phytopathology, 2004, 94: 1259-1266.
Lewis et al., "A total system approach to sustainable pest management", Proceedings of the National Academy of Science USA, 1997, 94: 12243-12248.
Pannucci et al., "Bacillus anthracis pXO1 plasmid sequence conservation among closely related bacterial species", Journal of Bacteriology, 2002, 184: 134-141.
Sorokulova et al., "Preclinical testing in the development of probiotics: a regulatory perspective with *Bacillus* strains as an example", Clinical Infectious Diseases, 2008, 46: SS92-95.
Welch, "IncA/C Plasmid-Mediated Florfenicol Resistance in the Catfish Pathogen Edwardsiella ictaluri", Antimicrobial Agents and Chemotherapy, 2008, 53: 845-846.
Wilson et al., "New transposon delivery plasmids for insertional mutagenesis in Bacillus anthracis", The Journal of Microbiological Methods, 2007, 71: 332-335.
Wise et al., "The relationship between vaccine dose and efficacy in channel catfish Ictalurus punctatus vaccinated as fry with a live attenuated strain of *Edwardsiella ictaluri* (Re-33)", Journal of the World Aquaculture Society, 2001, 32: 177-183.

(Continued)

*Primary Examiner* — S. Devi
(74) *Attorney, Agent, or Firm* — Andrus Intellectual Property Law, LLP

(57) ABSTRACT

Disclosed herein are microbiocidal compositions that include spore-forming strains of *Bacillus*. The compositions may be utilized to treat or prevent disease in aquatic animals such as farmed fish or crustaceans.

10 Claims, 7 Drawing Sheets

(56) References Cited

OTHER PUBLICATIONS

Zehnder et al., "Application of rhizobacteria for induced resistance", European Journal of Plant Pathology, 2001, 107:39-50.

Austin et al., "A probiotic strain of *Vibrio alginolyticus* effective in reducing diseases caused by Aeromonas salmonicida,Vibrio anguillarum and Vibrio ordalii", Journal of Fish Diseases, 1995, 18: 93-96.

Brunt et al., "Use of a probiotic to control lactococcosis and streptococcosis in rainbow trout, *Oncorhynchus mykiss* (Walbaum)", Journal of Fish Diseases, 2005, 28: 693-701.

Chang et al., "An evaluation of two probiotic bacterial strains, *Enterococcus faecium* SF68 and *Bacillus toyoi*, for reducing edwardsiellosis in cultured European eel, *Anguilla anguilla* L", Journal of Fish Diseases 2002, 25: 311-315.

Cipriano et al., "Aeromonas hydrophila and motile aeromonad septicemia of fish", U.S. Fish and Wildlife Service, Fish Disease Leaflet, 1984, 68:23.

Delbos et al., "Evaluation of a live attenuatedvaccine for the control of enteric septicemia of catfish under simulated production conditions", Aquaculture 2001: Book of Abstracts, 177.

Enebak et al., "Effects of plant growth-promoting rhizobacteria on loblolly and slash pine seedlings", Forest Science, 1998, 44:139-144.

Fuller et al., Bacteria associated with the intestinal wall of the fowl (*Gallus domesticus*). J Appl Bacteriol, 1971, 34: 617-622.

Fuller R., "A review: probiotics in man and animals", J Appl Bacteriol, 1989, 66: 365-378.

Gatesoupe, F.J., "The use of probiotics in aquaculture", Aquaculture, 1999, 180: 147-165.

Gaunt et al., "Preliminary Assessment of the Tolerance and Efficacy of Florfenicol against Edwardsiella ictaluri Administered in Feed to Channel Catfish", Journal of Aquatic Animal Health, 2003, 15(3), 239-247.

Gaunt et al., "Determination of Dose Rate of Florfenicol in Feed for Control of Mortality in Channel Catfish *Ictalurus punctatus* (Rafinesque) Infected with Edwardsiella ictaluri, Etiological Agent of Enteric Septicemia", Journal of the World Aquaculture Society, 2004, 35(2), 257-267.

Gildberg et al., "Effects of supplementing the feed to Atlantic cod(*Gadus morhua*) fry with lactic acid bacteria and immuno-stimulating peptides during a challenge trial with Vibrio anguillarum", Aquaculture, 1998, 167: 103-113.

Harikrishnan et al., "Hematological and biochemical parameters in common carp, *Cyprinus carpio*, following herbal treatment for Aeromonas hydrophila infection", Aquaculture, 2003, 221: 41-50.

Hawke, J. P., "A bacterium associated with disease of pond cultured channel catfish, *Ictalurus punctatus*", Journal of the Fisheries research Board of Canada, 1979, 36: 1508-1512.

Hawke et al., "*Edwardsiella ictaluri* sp. nov., the causative agent of enteric septicemia of catfish", International Journal of Systemic Microbiology, 1981, 31: 396-400.

Hawke et al., "Infectious diseases", Biology and Culture of Channel Catfish, 2004, ed. Tucker, C.S. and Hargreaves, J.A. pp. 387-443. Amsterdam, The Netherlands: Elsevier.

Hossain et al., "An outer membrane porin protein modulates phage susceptibility of Edwardsiella ictaluri", Microbiology, 2012 158(pt2):474-87, Epub 2011.

Irianto, et al., "Use of probiotics to control furunculosis in rainbow trout, *Oncorhynchus mykiss*(Walbaum)", Journal of Fish Diseases, 2002, 25: 333-342.

Joborn et al., "Colonization in the fish intestinal tract and production of inhibitory substances in intestinal mucus and faecal extracts by *Carnobacterium* sp. strain K1", Journal of Fish Diseases, 1997, 20: 383-392.

Johnson, M.R., "Bacterial resistance to antibiotics: a growing problem in the channel catfish industry", In: Proceedings of Louisiana Aquaculture Conference ed., 1991, Reigh, R.C., pp. 22-23. Louisiana State University Agricultural Center, Baton Rouge, LA.

Kenney, et al., "Mass production of biological agents for plant disease, weed and insect control", In: Biological Control in Crop Production BARC Symposium No. 5 ed.,1981, Papavizas, G.C., pp. 143-150. Totowa, NJ: Allenheld and Osmum.

Khoo, L., "Antibiotic resistance in the channel catfish industry", Aquaculture 2001: Book of Abstracts, 329.

Klesius, P. H., "Carrier state of channel catfish infected with Edwardsiella ictaluri", Journal of Aquatic Animal Health, 1992, 4(3), 227-230.

Kloepper et al., "Theory and applications of rhizobacteria for transplant production and yield enhancement", Proc. XXXVI IHC—Transplant Production and Stand Establishment, 2004, 631:217-229.

Kokalis-Burelle et al., "Amendment of muskmelon transplant media with plant growth-promoting rhizobacteria: effects on seedling quality, disease, and nematode resistance", Hortechnology, 2003, 13:476-482.

Lategan et al., "Control of saprolegniosis in the eel Anguilla australis Richardson, by *Aeromonas media* strain A199", Aquaculture, 2004, 240: 19-27.

Lim et al.,"Influence of Feed Deprivation on Hematology, Macrophage Chemotaxis, and Resistance to Edwardsiella ictaluri Challenge of Channel Catfish", Journal of Aquatic Animal Health, 2003, 15(1), 13-20.

Phan et al., "Current status of farming practices of striped catifish, *Pangasianodon hypophthalmus* in the Mekong Delta, Vietnam", Aquaculture, 2009, 296: 227-236.

Phuong et al., "Striped catfish (*Pangasianodon hypophthalmus*) aquaculture in Viet Nam: an unprecedented development within a decade", In: Success Stories in Asian Aquaculture ed., 2009, 133-149.

Plumb et al., "Susceptibility of six bacterial pathogens of channel catfish to six antibiotics", J Aquat Anim Health, 1995, 7: 211-217.

Plumb, J.A., "Edwardsiella septicaemias", In: Woo, P.T.K., and Bruno, D.W.[Eds.] Fish Diseases and disorders, 1999, 3: 479-521.

Pridgeon et al., "An in vitro screening method to evaluate chemicals as potential chemotherapeutants to control Aeromonas hydrophila infection in channel catfish", J Appl Microbiol, 2011, 111: 114-124.

Queiroz et al., "Effects of a Bacterial Inoculum in Channel Catfish Ponds", J World Aquacult Soc, 1998, 29: 67-73.

Rengpipat et al., "Effects of a probiotic bacterium on black tiger shrimp Penaeus monodon survival and growth", Aquaculture, 1998, 167: 301-313.

Rhaman et al., "The effect of temperature on Aeromonas hydrophila infection in goldfish, *Carassius auratus*", J Appl Ichthyol, 2001, 17: 282-285.

Roach et al., "Indigenous bacteria that influence the Number of *Salmonella typhimurium* in the spleen of intravenously challenged mice", Can J Microbiol, 1980, 26: 408-411.

Robertson et al., "Use of *Carnobacterium* sp. as a probiotic for Atlantic salmon (*Salmo salar* L.) and rainbow trout (*Oncorhynchus mykiss*, Walbaum)", Aquaculture, 2000, 185: 235-243.

Sanchis et al., "Bacillus thuringiensis: applications in agriculture and insect resistance management. A review.", Agronomy for Sustainable Development, 2008, 28:11-20.

Serageldin, I. "Biotechnology and food security in the 21st century", Science, 1999, 285:387-389.

Shoemaker et al.,"Eficacy of a modified live Edwardsiella ictaluri vaccine in channel catfish as young as seven days post hatch", Aquaculture, 1999, 176: 189-193.

Smoragiewicz et al., "Les probiotiques", Can J Microbiol, 1993, 39: 1089-1095.

Sugita et al., "The vitamin B12-producing ability of intestinal bacteria isolated from tilapia and channel catfish", Nippon Suisan Gakkaishi, 1990, 56: 701.

Tang et al., "Cloning and heterologous expression of the epothilone gene cluster", Science, 2000, 287:640-642.

USDA. Part I: "Reference of Fingerling Catfish Health and Production Practices in the United States", Fort Collins, CO#N406.1103, USDA:APHIS:VS:CEAH, National Animal Health Monitoring System, 2003a.

USDA. Part II: "Reference of Foodsize Catfish Health and Production Practices in the United States", Fort Collins, CO #N407.1103, USDA:APHIS:VS:CEAH, National Animal Health Monitoring System, 2003b.

Wagner et al., "The epidemiology of bacterial diseases in food-size channel catfish", J Aquat Anim Health, 2002, 14: 263-272.

(56) References Cited

OTHER PUBLICATIONS

Walakira et al., "Identification and characterization of bacteriophages specific to the catfish pathogen *Edwardsiella ictaluri*", Journal of Applied Microbiology, 2007, 105(6):2133-2142.

Weisburg et al., "16S Ribosomal DNA Amplification for Phylogenetic Study", J Bacteriol, 1991, 173: 697-703.

Wise et al., "Effect of feeding frequency and Romet-medicated feed on survival, antibody response, and weight gain of fingerling channel catfish Ictalurus punctatus after natural exposure to Edwardsiella ictaluri", Journal of the World Aquaculture Society, 1998, 29: 169-175.

Wise et al., Vaccination of mixed and full-sib families of channel catfish Ictalurus punctatus after natural exposure to Edwardsiella ictaluri, Journal of the World Aquaculture Society, 2000, 31: 206-212.

Abriouel et al., "Diversity and Application of Bacillus Bacteriocins", Microbiology Reviews, 2011, 35(1): 201-232.

Chang et al., "An Evaluation of Two Probiotic Bacterial Strains, *Enterococcus faecium* SF68 and *Bacillus toyoi*, for Reducing Edwardsiellosis in Cultured European Eel, *Anguilla anguilla* L", Journal of Fish Diseases, 2002, 25(5): 311-315.

Database EMBL, Database Accession No. AY462201 "*Bacillus* Sp. DF15 16S Ribosomal RNA Gene, Partial Sequence", Dec. 31, 2004.

Database EMBL, Database Accession No. DQ683077, "*Bacillus subtilis* Strain GB03 16S Ribosomal RNA Gene, Partial Sequence", Jul. 23, 2006.

International Search Report, PCT International Application No. PCT/US2012/035841, mailed Feb. 11, 2013.

Written Opinion, PCT International Application No. PCT/US2012/035841, mailed Feb. 11, 2013.

Abriouel et al., "Diversity and applications of Bacillus bacteriocins", FEMS Microbiol Rev, 2011, 35:201-232.

Chang et al., "An evaluation of two probiotic bacterial strains, *Enterococcus faecium* SF68 and *Bacillus toyoi*, for reducing edwardsiellosis in cultrured European eel, *Anguilla anguilla* L", Journal of Fish Diseases, 2002, 25:311-315.

Database EMBL, "*Bacillus subtilis* strain GB03 16S ribosomal RNA gene, partial sequence", XP002679809, Jul. 23, 2006, and Salinas et al., "Bacterial preferences of the bacteriovorous soil nematode *Cephalobus brevicauda* (Cephalobidae): Effect of bacterial type and size", Mar. 13, 2007, 51(1):55-64.

Database EMBL, "*Bacillus* sp. DF15 16S ribosomal RNA gene, partial sequence", XP002679814, Dec. 31, 2004.

Invitation to Pay Additional Fees and, Where Applicable, Protest Fee and Annex Communication Relating to the Results of the Partial International Search for PCT/US2012/035841 dated Aug. 1, 2012.

English Abstract for WO2004044186, published May 27, 2004.

International Preliminary Report on Patentability for PCT/US2012/035841 dated Nov. 7, 2013.

Aly et al., "Studies on Bacillus subtilis and Lactobacillus acidophilus, as potential probiotics, on the immune response and resistance of Tilapio nilotica (*Oreochromis niloticus*) to challenge infections", Shellfish Immunology, 2008, 25: 128-136.

Carrias, "Evaluation of Biological Agents for Controlling Enteric Septicemia of Catfish", Auburn University Dissertation, May 9, 2011.

Liqun et al., "The potential of a *Bacillus* strain as the biological source of pharmaceutical compound against Saprolegniasis", Fishery Modernization, Dec. 2010, 38(4):31-34.

Office Action for Chinese Application No. 201280027776.1 dated Dec. 26, 2014.

Office Action for European Application No. 12723773.3 dated Sep. 8, 2014.

Cho et al., "Molecular differentiation of *bacillus* spp. antagonistic against phytopathogenic fungi causing damping-off disease", Journal of Microbiology and Biotechnology, 2004, 14(3):599-606.

Examiner's Report for CA2,834,382 dated Jun. 17, 2015.

\* cited by examiner

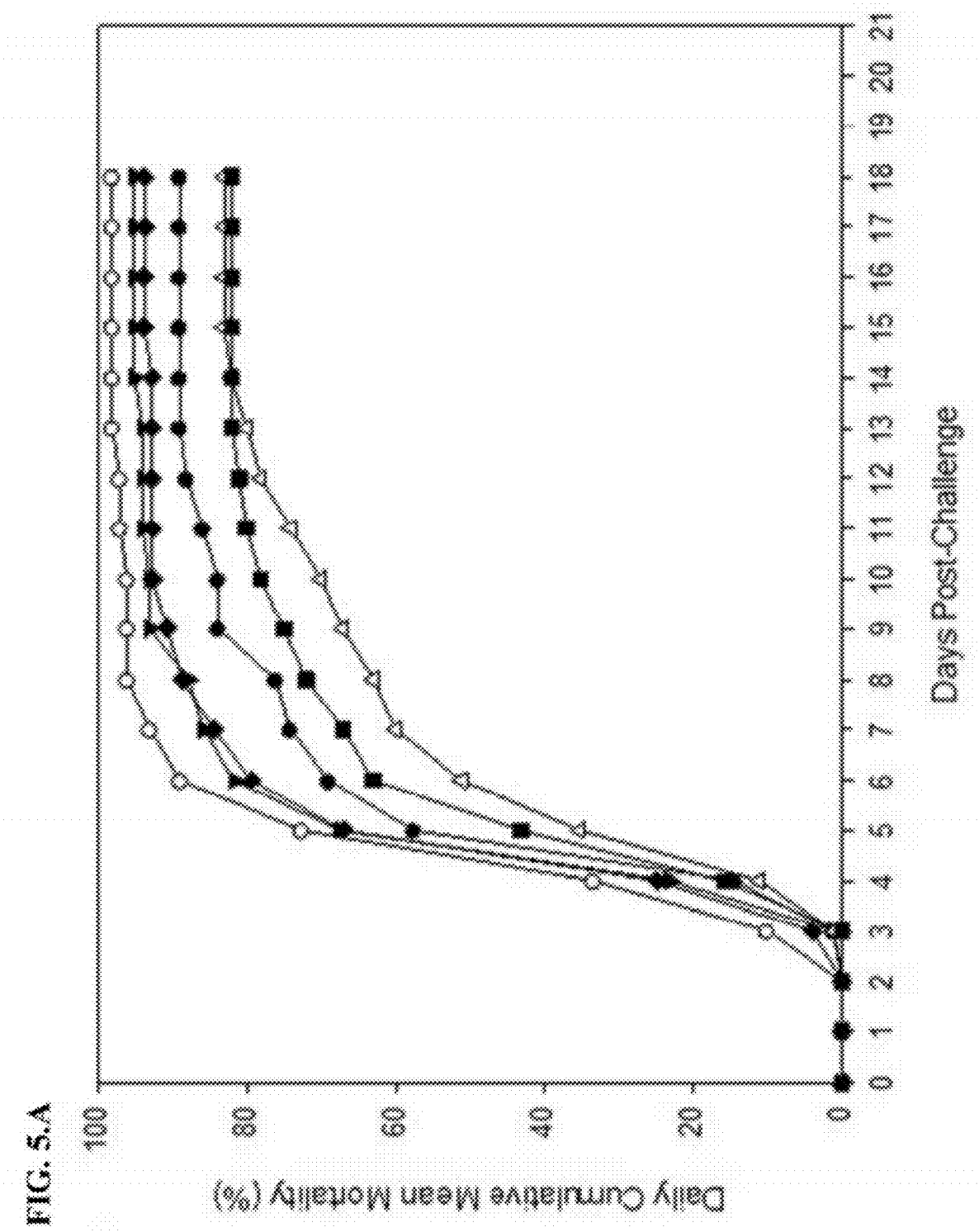

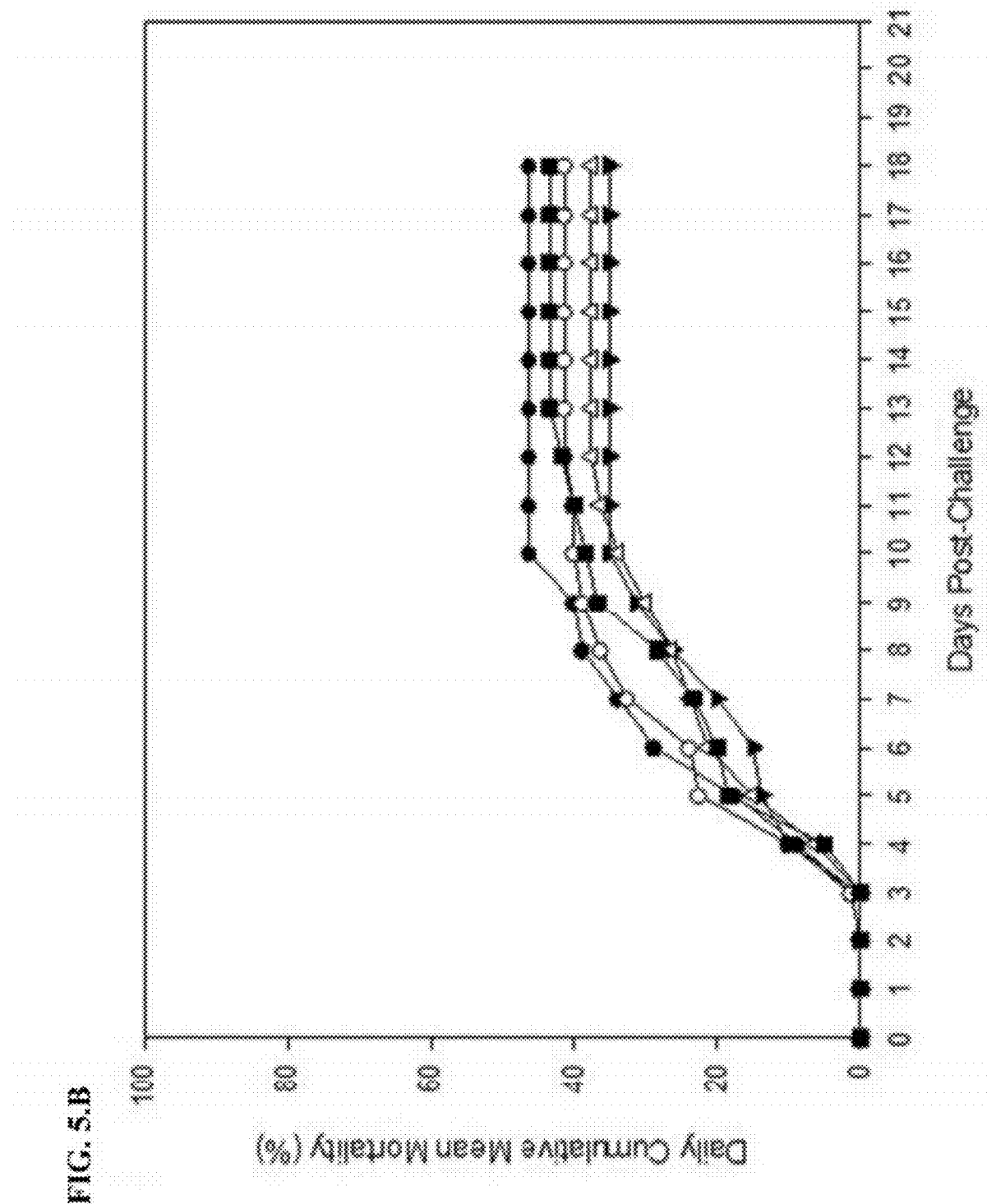
FIG. 5.B

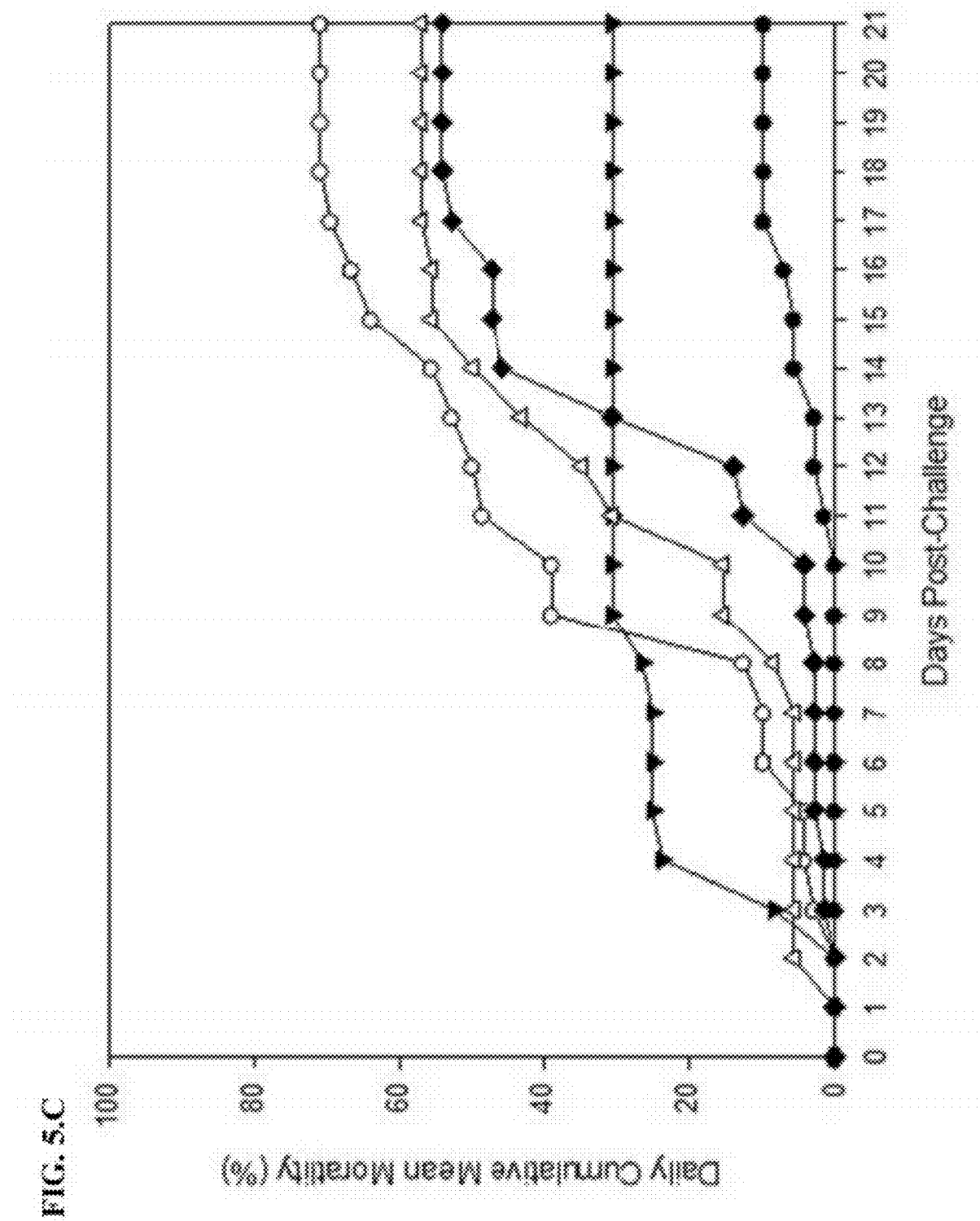
FIG. 5.C

SEQUENCE LISTING

<160> NUMBER OF SEQ ID NOS: 3

<210> SEQ ID NO 1
<211> LENGTH: 1124
<212> TYPE: DNA
<213> ORGANISM: Bacillus subtilis

<400> SEQUENCE: 1

```
tgctatacat gcaagtcgag cggacagatg ggagcttgct ccctgatgtt agcggcggac        60
gggtgagtaa cacgtgggta acctgcctgt aagactggga taactccggg aaaccggggc       120
taataccgga tggttgtttg aaccgcatgg ttcagacata aaaggtggct tcggctacca       180
cttacagatg gacccgcggc gcattagcta gttggtgagg taacggctca ccaaggcgac       240
gatgcgtagc cgacctgaga gggtgatcgg ccacactggg actgagacac ggcccagact       300
cctacgggag gcagcagtag ggaatcttcc gcaatggacg aaagtctgac ggagcaacgc       360
cgcgtgagtg atgaaggttt tcggatcgta aagctctgtt gttagggaag aacaagtgcc       420
gttcaaatag gcggcaccct tgacggtacc taaccagaaa gccacggcta actacgtgcc       480
agcagccgcg gtaatacgta ggtggcaagc gttgtccgga attattgggc gtaaagggct       540
cgcaggcggt ttcttaagtc tgatgtgaaa gcccccggct caaccgggga gggtcattgg       600
aaactgggga acttgagtgc agaagaggag agtggaattc cacgtgtagc ggtgaaatgc       660
gtagagatgt ggaggaacac cagtggcgaa ggcgactctc tggtctgtaa ctgacgctga       720
ggagcgaaag cgtggggagc gaacaggatt agataccctg gtagtccacg ccgtaaacga       780
tgagtgctaa gtgttagggg gtttccgccc cttagtgctg cagctaacgc attaagcact       840
ccgcctgggg agtacggtcg caagactgaa actcaaagga attgacgggg cccgcacaa       900
gcggtggagc atgtggttta attcgaagca acgcgagaac cttaccaggt cttgacatcc       960
tctgacatcc tagagatagg acgtcccctt cggggggcaga gtgacagtgg tgcatggttg      1020
tcgtcagctc gtgtcgtgag atgttgggta agtcccgcac gagcgcaccc ttgatcttag      1080
ttgccagcat tcagttggca ctctaaggtg actgccggtg acga                       1124
```

<210> SEQ ID NO 2
<211> LENGTH: 1577
<212> TYPE: DNA
<213> ORGANISM: Bacillus amyloliquefaciens

<400> SEQUENCE: 2

```
gatcctggct caggacgaac gctggcggcg tgcctaatac atgcaagtcg agcggacaga        60
tgggagcttg ctccctgatg ttagcggcgg acgggtgagt aacacgtggg taacctgcct       120
gtaagactgg gataactccg ggaaaccggg gctaataccg gatggttgtc tgaaccgcat       180
```

```
ggttcagaca taaaaggtgg cttcggctac cacttacaga tggacccgcg gcgcattagc      240
tagttggtga ggtaacggct caccaaggcg acgatgcgta gccgacctga gagggtgatc      300
ggccacactg ggactgagac acggcccaga ctcctacggg aggcagcagt agggaatctt      360
ccgcaatgga cgaaagtctg acggagcaac gccgcgtgag tgatgaaggt tttcggatcg      420
taaagctctg ttgttaggga agaacaagtg ccgttcaaat agggcggcac cttgacggta      480
cctaaccaga aagccacggc taactacgtg ccagagccgc gggtaatacg taggtggcaa      540
gcgttgtccg gaattattgg gcgtaaaggg ctcgcaagcg ttttcttaag tctgatgtga      600 aaccccccggg ctcaaccggg gagggtcatt ggaaaccgag gaacttgagt gcagaagagg      660
agagtggaat tccacgtgta gcggtgaaat gcgtagagat gtggaggaac accagtggcg      720
aaggcgactc tctgttctgt aactgacgct gagagagcga agcgtgggga gcgaacagaa      780 ttagatacccc tggtagtcca cgccgtaaac gatgagtgct aagtgttagg gggtttccgc      840
cccttagtgc tgcagctaac gcattaagca ctccgcctgg ggagtacggt cgcaagactg      900
aaactcaaag gaattgacgg gggcccgcac aagcggtgga gcatgtggtt taattcgaag      960
caacgcgaag aaccttacca ggtcttgaca tcctctgaca atcctagaga taggacgtcc     1020
ccttcggggg cagagtgaca ggtggtgcat ggttgtcgtc agctcgtgtc gtgagatgtt     1080
gggttaagtc ccgcaacgag cgcaacccctt gatcttagtt gccagcattc agttgggcac     1140
tctaaggtga ctgccggtga caaaccggag gaaggtgggg atgacgtcaa atcatcatgc     1200
cccttatgac ctgggctaca cacgtgctac aatggacaga acaaagggca gcgaaaccgc     1260
gaggttaagc caatcccaca aatctgttct cagttcggat cgcagtctgc aactcgactg     1320
cgtgaagctg gaatcgctag taatcgcgga tcagcatgcc gcggtgaata cgttcccggg     1380
ccttgtacac accgcccgtc acaccacgag agtttgtaac acccgaagtc ggtgaggtaa     1440
cctttatgga gccagccgcc gaaggtggga cagatgattg gggtgaagtc gtaacaaggt     1500
agccgtatcg gaaggtgcgg ctggatcacc tcctttctaa ggattttaac ggaatataag     1560
accttgggtc ttataac                                                    1577
```

<210> SEQ ID NO 3
<211> LENGTH: 722
<212> TYPE: DNA
<213> ORGANISM: Artificial
<220> FEATURE:
<223> OTHER INFORMATION: Consensus sequence for Bacillus spp. 16S rDNA

<400> SEQUENCE: 3

```
acacttagca ctcatcggtt tacggcgtgg actaccaggg tatctaatcc tgttcgctcc       60
ccacgctttc gctcctcagc gtcagttaca gaccagagag tcgccttcgc cactggtgtt      120
cctccacatc tctacgcatt tcaccgctac acgtggaatt ccactctcct cttctgcact      180
caagttcccc agtttccaat gaccctcccc ggttgagccg ggggctttca catcagactt      240
aagaaaccgc ctgcgagccc tttacgccca ataattccgg acaacgcttg ccacctacgt      300
attaccgcgg ctgctggcac gtagttagcc gtggctttct ggttaggtac cgtcaaggtg      360 ccgcccctatt tgaacggcac ttgttcttcc ctaacaacag agctttacga tccgaaaacc      420
ttcatcactc acgcggcgtt gctccgtcag actttcgtcc attgcggaag attccctact      480
gctgcctccc gtaggagtct gggccgtgtc tcagtcccag tgtggccgat cacccctctca      540 ggtcggctac gcatcgtcgc cttggtgagc cgttacctca ccaactagct agtgcgccgc      600
```

```
gggtccatct gtaagtggta gccgaagcca cctttatgt ctgaaccatg cggttcaaac        660
aaccatccgg tattagcccc ggtttcccgg atgttatccc catgtcttag cagggcaggg        720
tt                                                                       722
```

BACILLUS BACTERIA FOR USE IN TREATING AND PREVENTING INFECTION IN AQUATIC ANIMALS

CROSS-REFERENCE TO RELATED APPLICATIONS

The present application claims the benefit of priority under 35 U.S.C. §119(e) to U.S. Provisional Applications No. 61/480,622, filed on Apr. 29, 2011, the content of which is incorporated herein by reference in its entirety.

BACKGROUND

The field of the present invention relates to compositions and methods for treating or preventing disease in aquatic animals such as farmed fish (e.g. catfish or tilapia) and crustaceans (e.g., shrimp). In particular, the present invention relates to compositions and methods comprising or utilizing spore forming strains of *Bacillus* for treating or preventing diseases such as enteric septicemia in aquatic animals such as farmed fish (e.g. catfish or tilapia) and crustaceans (e.g., shrimp).

Recently, attention has focused on the use of probiotics to improve animal health and nutrition. The interest in probiotic bacteria for aquaculture application follows their use in human medicine and agriculture (Fuller and Turvey 1971; Roach and Tannock 1980; Fuller 1987; Smoragiewicz et al. 1993; Fuller 1997), in which microorganisms are generally administered as live supplements in feed (Fuller 1997). The beneficial effect to the host has been reported to be nutritional, immunological, and/or to involve competitive exclusion whereby potential pathogens are outcompeted in the digestive tract (Smoragiewicz et al. 1993). Probiotics have been shown to be effective in controlling various infectious diseases in aquaculture, including furunculosis caused by *A. salmonicida* in rainbow trout (Irianto and Austin 2002), saprolegniosis by *Saprolegnia parasitica* in the short-finned eel *Anguilla australis* (Lategan et al. 2004), edwardsiellosis by *Edwardsiella tarda* in the European eel *Anguilla anguilla* (Chang and Liu 2002), lactococcosis and streptococcosis by *Lactococcus garvieae* and *Streptococcus iniae*, respectively, in rainbow trout (Brunt and Austin 2005), and disease caused by *Vibrio anguillarum* in Atlantic cod fry (Gildberg and Mikkelsen 1998). The bacteria used for probiotics include *Enterococcus* spp., *Aeromonas* spp., *Vibrio* spp., and lactic acid bacteria (Gildberg and Mikkelsen 1998; Chang and Liu 2002; Irianto and Austin 2002; Lategan et al. 2004; Brunt and Austin 2005). Most of the probiotic bacteria were isolated from the intestine of aquaculture animals (Gildberg and Mikkelsen 1998; Irianto and Austin 2002; Lategan et al. 2004; Brunt and Austin 2005). Some bacteria isolated from the habitats of aquaculture animals also showed probiotic activity (Rengpipat et al. 1998). The antimicrobial activity against a particular pathogen is used as a primary criterion for selection of potential probiotic bacteria (Rengpipat et al. 1998; Irianto and Austin 2002). The collection of bacterial strains used in this study was derived from previous studies of soil-derived bacteria useful for biological control of diseases in plants and for their plant growth-promoting abilities (Kloepper et al. 2004), as well as bacterial cultures derived from catfish intestinal samples identified in this study.

SUMMARY

Disclosed are microbiocidal compositions that kill or inhibit the growth of bacteria. The composition may kill or inhibit the growth of pathogenic bacteria such as bacteria associated with enteric septicemia. The compositions comprise an effective amount of a spore-forming strain of *Bacillus* for killing or inhibiting the growth of bacteria, such as bacteria associated with enteric septicemia. In some embodiments, the disclosed compositions are formulated as feed compositions for aquatic animals such as farmed fish (e.g. catfish or tilapia) and crustaceans (e.g., shrimp). In other embodiments, the disclosed compositions may be formulated for administering to an environment where aquatic animals live or are raised.

Preferably, the compositions comprise a spore-forming strain of the genus *Bacillus* at a concentration of at least about $10^4$ CFU/g of feed or per ml of water. More preferably, the spore-forming strain of the genus *Bacillus* is present in the composition at a concentration of at least about $10^5$ CFU/g of feed or per ml of water. Even more preferably, the spore-forming strain of the genus *Bacillus* is present in the composition at a concentration of at least about $10^6$ CFU/g of feed or per ml of water or at least about $10^7$ CFU/g of feed or per ml of water. A suitable concentration range may include $10^4$-$10^7$ CFU/g of feed or per ml of water or sub-ranges there within.

The compositions may comprise a single strain of the genus *Bacillus*. Alternatively, the compositions may comprise a mixture of strains of the genus *Bacillus*.

The compositions typically comprise an effective amount the spore-forming strain of the genus *Bacillus* to kill or inhibit the growth of one or more pathogenic microorganism. For example, pathogenic bacteria may be selected from a group consisting of *Aeromonas hydrophila*, *Edwardsiella ictaluri*, *Edwardsiella tarda*, *Flavobacterium columnare*, *Streptococcus iniae*, and *Yersinia ruckeri*. Pathogenic fungi may include the oomycete fungus *Saprolegnia*.

The disclosed compositions comprise a spore-forming strain of *Bacillus*. The compositions may comprise further agents for killing or preventing the growth of pathogenic microorganisms. In some embodiments, the compositions further comprise a bacteriophage that infects *E. ictaluri* (e.g., φeiAU). The disclosed compositions may comprise antibiotic agents such as sulfadimethoxine, ormetoprim, and/or florfenical. The disclosed compositions further may comprise an attenuated microbe as a vaccine agent (e.g., an attenuated strain of *E. ictaluri*).

Also disclosed are methods for treating or preventing disease in an animal comprising administering the presently disclosed compositions. For example, the methods may include administering a feed composition comprising a spore-forming strain of *Bacillus* to aquatic animals such as farmed fish (e.g. catfish or tilapia) and crustaceans (e.g., shrimp). The methods further may include administering a microbiocidal composition as disclosed herein to an environment where aquatic animals such as farmed fish (e.g. catfish or tilapia) and crustaceans (e.g., shrimp) live and/or are raised. The methods may be utilized to treat or prevent diseases such as enteric septicemia. The method may be utilized to treat or prevent infection in aquatic animals such as farmed fish (e.g. catfish or tilapia) and crustaceans (e.g., shrimp) by pathogenic microorganisms such as *Aeromonas hydrophila*, *Edwardsiella ictaluri*, *Edwardsiella tarda*, *Flavobacterium columnare*, *Streptococcus iniae*, *Yersinia ruckeri*, *Vibrio* species and/or the oomycete fungus *Saprolegnia*.

BRIEF DESCRIPTION OF THE DRAWINGS

FIG. 5. Illustrates the daily mean cumulative mortality of (A) channel catfish in static system with 20-30 min daily water exchange and (B) channel catfish with 5-7 h flow through water daily, or (C) striped catfish in static system with 20-30 min daily water exchange, fed with and without addition of *Bacillus* strains and challenged with *E. ictaluri*. All values are means of four replicates per treatment. Treatments: (○) Control, (●) AP79, (▼) AP193L, (Δ) AB01, (■) AP143, and (♦) AP254L.

DETAILED DESCRIPTION

Figure 1:
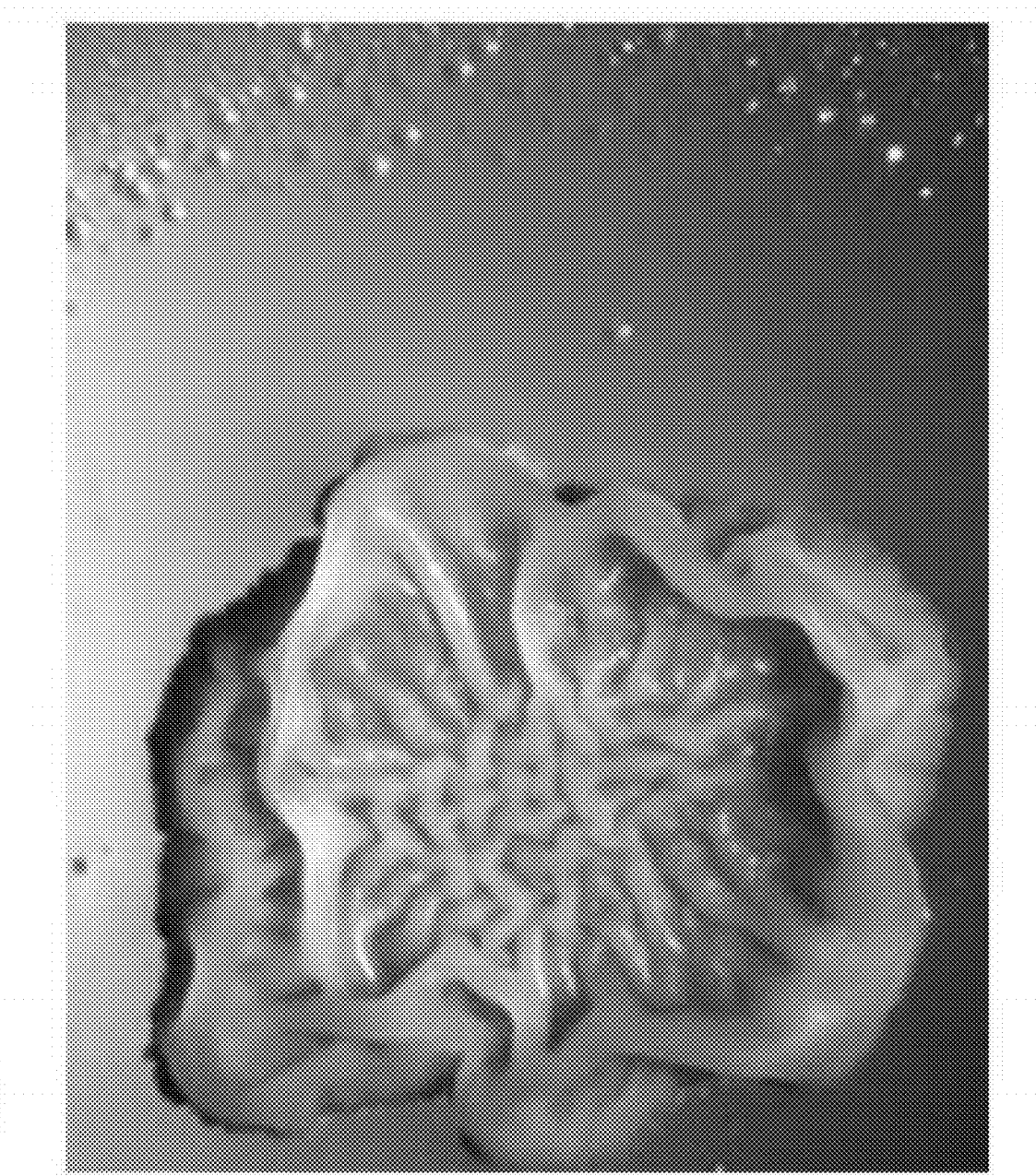
FIG. 1 illustrates a photomicrograph at 10× magnification of a soft agar overlay demonstrating growth inhibition of *A. hydrophila* strain ML09-119 (on the right) by *Bacillus* strain AP102 (on the left).

Disclosed herein are microbiocidal compositions. The disclosed microbiocidal compositions may be described using several definitions as discussed below.

Unless otherwise specified or indicated by context, the terms "a", "an", and "the" mean "one or more." In addition, singular nouns such as "a strain of *Bacillus*" should be interpreted to mean "one or more strains of *Bacillus*," unless otherwise specified or indicated by context.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus≤10% of the particular term and "substantially" and "significantly" will mean plus or minus>10% of the particular term.

As used herein, the terms "include" and "including" have the same meaning as the terms "comprise" and "comprising."

The presently disclosed composition and methods include or utilize a spore-forming strain of the *Bacillus* genus. The genus *Bacillus* as used herein refers to a genus of Gram-positive, rod-shaped bacteria which are members of the division Firmicutes. Under stressful environmental conditions, the *Bacillus* bacteria produce oval endospores that can stay dormant for extended periods. *Bacillus* bacteria may be characterized and identified based on the nucleotide sequence of their 16S rRNA or a fragment thereof (e.g., approximately a 1000 nt, 1100 nt, 1200 nt, 1300 nt, 1400 nt, or 1500 nt fragment of 16S rRNA or rDNA nucleotide sequence). *Bacillus* bacteria may include, but are not limited to *B. acidiceler, B. acidicola, B. acidiproducens, B. aeolius, B. aerius, B. aerophilus, B. agaradhaerens, B. aidingensis, B. akibai, B. alcalophilus, B. algicola, B. alkalinilrilicus, B. alkalisediminis, B. alkalitelluris, B. altitudinis, B. alveayuensis, B. amyloliquefaciens, B. anthracis, B. aquimaris, B. arsenicus, B. aiyabhattai, B. asahii, B. atrophaeus, B. aurantiacus, B. azotoformans, B. badius, B. barbaricus, B. bataviensis, B. beijingensis, B. benzoevorans, B. beveridgei, B. bogoriensis, B. boroniphilus, B. butanolivorans, B. canaveralius, B. carboniphilus, B. cecembensis, B. cellulosilylicus, B. cereus, B. chagannorensis, B. chungangensis, B. cibi, B. circulars, B. clarkii, B. clausii, B. coagulans, B. coahuilensis, B. cohnii, B. decisifrondis, B. decolorationis, B. drentensis, B. farraginis, B. fastidiosus, B. firmus, B. flexus, B. foraminis, B. fordii, B. fortis, B. fumarioli, B. funiculus, B. galactosidilyticus, B. galliciensis, B. gelatini, B. gibsonii, B. ginsengi, B. ginsengihumi, B. graminis, B. halmapalus, B. halochares, B. halodurans, B. hemicellulosilyticus, B. herberisteinensis, B. horikoshi, B. horneckiae, B. horti, B. humi, B. hwajinpoensis, B. idriensis, B. indicus, B. infantis, B. infernus, B. isabeliae, B. isronensis, B. jeotgali, B. koreensis, B. korlensis, B. kribbensis, B. krulwichiae, B. lehensis, B. lentus, B. licheniformis, B. litoralis, B. locisalis, B. luciferensis, B. luteolus, B. macauensis, B. macyae, B. mannanilyticus, B. marisflavi, B. marmarensis, B. massiliensis, B. megaterium, B. methanolicus, B. methylotrophicus, B. mojavensis, B. muralis, B. murimartini, B. mycoides, B. nanhaiensis, B. nanhaiisediminis, B. nealsonii, B. neizhouensis, B. niabensis, B. niacini, B. novalis, B. oceanisediminis, B. odysseyi, B. okhensis, B. okuhidensis, B. oleronius, B. oshimensis, B. panaciterrae, B. patagoniensis, B. persepolensis, B. plakortidis, B. pocheonensis, B. polygoni, B. pseudoalcaliphilus, B. pseudofirmus, B. pseudomycoides, B. psychrosaccharolyticus, B. pumilus, B. qingdaonensis, B. rigui, B. ruris, B. safensis, B. salarius, B. saliphilus, B. schlegelii, B. selenatarsenatis, B. selenitireducens, B. seohaeanensis, B. shackletonii, B. siamensis, B. simplex, B. siralis, B. smithii, B. soli, B. solisalsi, B. sonorensis, B. sporothermodurans, B. stratosphericus, B. subterraneus, B. subtilis, B. taeansis, B. tequilensis, B. thermantarcticus, B. thermoamylovorans, B. thermocloacae, B. thermolactis, B. thioparans, B. thuringiensis, B. tripoxylicola, B. tusciae, B. vallismortis, B. vedderi, B. vietnamensis, B. vireti, B. wakoensis, B. weihenstephanensis, B. xiaoxiensis*, and mixtures or blends thereof.

The disclosed compositions and methods may include or utilize *B. subtilis* or a *Bacillus* species that is closely related to *B. subtilis*. The partial sequence of *B. subtilis* strain NH.259 16S ribosomal rDNA (GenBank Accession No. EU627171.1) is provided herein as SEQ ID NO:1. A *Bacillus* species that is closely related to *B. subtilis* may be defined as a species comprising a 16S rDNA sequence comprising SEQ ID NO:1 or comprising a 16S rDNA sequence having at least about 90%, 91%, 92%, 93%, 94%, 95%, 96%, 97%, 98%, or 99% sequence identity to SEQ ID NO:1.

The disclosed compositions and methods may include or utilize *B. amyloliquefaciens* or a *Bacillus* species that is closely related to *B. amyloliquefaciens*. The partial sequence of *B. amyloliquefaciens* strain Chilli-1 16S ribosomal rDNA (GenBank Accession No. HQ021420.1) is provided herein as SEQ ID NO:2. A *Bacillus* species that is closely related to *B. amyloliquefaciens* may be defined as a species comprising a 16S rDNA sequence comprising SEQ ID NO:2 or comprising a 16S rDNA sequence having at least about 90%, 91%, 92%, 93%, 94%, 95%, 96%, 97%, 98%, or 99% sequence identity to SEQ ID NO:2.

The disclosed compositions and methods may include or utilize a *Bacillus* species that has a 16S rDNA closely related to a selected consensus sequence for *Bacillus* spp. strains. A consensus sequence for *Bacillus* spp. strains is provided as SEQ ID NO:3. The disclosed compositions and methods may include or utilize a *Bacillus* species that comprises a 16S rDNA sequence comprising SEQ ID NO:3 or comprising a 16S rDNA sequence having at least about 90%, 91%, 92%, 93%, 94%, 95%, 96%, 97%, 98%, or 99% sequence identity to SEQ ID NO:3.

"Percentage sequence identity" may be determined by aligning two sequences of equivalent length using the Basic Local Alignment Search Tool (BLAST) available at the National Center for Biotechnology Information (NCBI) website (i.e., "bl2seq" as described in Tatiana A. Tatusova, Thomas L. Madden (1999), "Blast 2 sequences—a new tool for comparing protein and nucleotide sequences", FEMS Microbiol Lett. 174:247-250, incorporated herein by reference in its entirety). For example, percentage sequence identity between SEQ ID NO:1, SEQ ID NO:2, or SEQ ID NO:3 may be determined by aligning these two sequences using the online BLAST software provided at the NCBI website.

"Percentage sequence identity" between two deoxyribonucleotide sequences may also be determined using the Kimura 2-parameter distance model which corrects for multiple hits, taking into account transitional and transversional substitution rates, while assuming that the four nucleotide frequencies are the same and that rates of substitution do not vary among sites (Nei and Kumar, 2000) as implemented in the MEGA 4 (Tamura K, Dudley J, Nei M & Kumar S (2007) MEGA4: Molecular Evolutionary Genetics Analysis (MEGA) software version 4.0. *Molecular Biology and Evolution* 24:1596-1599), preferably version 4.0.2 or later. The gap opening and extension penalties are set to 15 and 6.66 respectively. Terminal gaps are not penalized. The delay divergent sequences switch is set to 30. The transition weight score is 35 set to 0.5, as a balance between a complete mismatch and a matched pair score. The DNA weight matrix used is the IUB scoring matrix where x's and n's are matches to any IUB ambiguity symbol, and all matches score 1.9, and all mismatched score O.

Suitable strains of *Bacillus* for the disclosed compositions and methods include strains disclosed in the Examples provided herein. These suitable strains include, but are not limited to *Bacillus subtilis* strain AB01, and *Bacillus amyloliquefaciens* strains AP79, AP143, AP193L, and AP254L, deposited at the United Stated Department of Agriculture on Apr. 27, 2012, under accession numbers NRRL B-50745, NRRL B-50741, NRRL B-50742, and NRRL B-50743, and NRRL B-50744, respectively.

The presently disclosed strains of *Bacillus* exhibit antibiotic activity in various bacterial pathogens of aquatic animals such as farmed fish (e.g. catfish or tilapia) and crustaceans (e.g., shrimp) including species of *Edwardsiella* bacteria such as *Edwardsiella ictaluri*. In some embodiments, the disclosed bacteriophage or variants thereof may be utilized in methods for killing or preventing the growth of pathogenic bacteria or fungi of aquatic animals such as farmed fish (e.g. catfish or tilapia) and crustaceans (e.g., shrimp). In particular, the methods may be utilized to control or prevent the infection or colonization of catfish (e.g., *Ictaluri punctatus* Rafinesque) by pathogenic bacteria or fungi or colonization of environments in which catfish live or are raised (e.g., aquaculture ponds). The disclosed methods also may be utilized to detect the presence of bacteria in a sample (e.g., a sample obtained from infected aquatic animals such as farmed fish (e.g. catfish or tilapia) and crustaceans (e.g., shrimp), or a sample isolated from an environment in which aquatic animals such as farmed fish (e.g. catfish or tilapia) and crustaceans (e.g., shrimp) live or are raised).

Also disclosed are methods of using the disclosed strains of *Bacillus* for removing pathogenic bacteria or fungi from environments or instruments used to raise aquatic animals such as farmed fish (e.g. catfish or tilapia) and crustaceans (e.g., shrimp), thereby reducing the likelihood that the bacteria or fungi may be passed to the aquatic animals such as farmed fish (e.g. catfish or tilapia) and crustaceans (e.g., shrimp).

Also disclosed are methods of using the presently disclosed strains of *Bacillus* to treat or prevent diseases caused by pathogenic bacteria or fungi (e.g., treating or preventing enteric septicemia of catfish (ESC)). In further embodiments, in order to control or inhibit the growth of pathogenic bacteria or fungi or to remove pathogenic bacteria or fungi, the presently disclosed strains of *Bacillus* may be administered to an environment (e.g., a pond) or instrument, or the presently disclosed strains of *Bacillus* may be administered to aquatic animals such as farmed fish (e.g. catfish or tilapia) and crustaceans (e.g., shrimp).

The term "catfish" refers to a fish belonging to the genus *Ictaluri*. Catfish may include the species *Ictaluri punctatus* Rafinesque.

The presently disclosed strains of spore-forming *Bacillus* may be utilized to kill or prevent the growth of bacteria or fungi that are pathogenic to aquatic animals such as farmed fish (e.g. catfish or tilapia) and crustaceans (e.g., shrimp). "Pathogenic bacteria" may include, but are not limited to, *A. hydrophila, E. ictaluri, E. tarda, F. columnare, Streptococcus iniae, F. columnare, Yersinia ruckeri*, and *Vibrio* species. "Pathogenic fungi may include, but are not limited to the oomycete fungus *Saprolegnia*.

The disclosed strains of spore-forming *Bacillus* may be administered with additional agents for killing or preventing the growth of pathogenic bacteria or fungi. Additional agents may include antibiotics such as sulfadimethoxine and ormetoprim, attenuated strains of bacteria (e.g., an attenuated strain of *E. ictaluri*), florfenical, and bacteriophage. Bacteriophage may include the bacteriophage designated as ΦeiAU, deposited with the American Type Culture Collection (ATCC), located at 10801 University Boulevard, Manassas, Va., 20110-2209, USA, on Sep. 15, 2009 under accession no. PTA-10342.

The term "sample" is used herein in its broadest sense. A sample may comprise a biological sample from an animal (e.g., a biological sample obtained from aquatic animals such as farmed fish (e.g. catfish or tilapia) and crustaceans (e.g., shrimp)) or a sample taken from an environment (e.g., a water sample from a pond or a swabbed surface sample taken from a container or instrument).

ILLUSTRATIVE EMBODIMENTS

The following embodiments are illustrative and are not intended to limit the claimed subject matter.

Embodiment 1. A feed composition comprising one or more spore-forming strains of the genus *Bacillus*.

Embodiment 2. The composition of embodiment 1, wherein the spore-forming strain of the genus *Bacillus* is *Bacillus subtilis* or a *Bacillus* species comprising a 16S rDNA sequence comprising SEQ ID NO:1 or comprising a 16S rDNA sequence having at least about 90%, 91%, 92%, 93%, 94%, 95%, 96%, 97%, 98%, or 99% sequence identity to SEQ ID NO: 1.

Embodiment 3. The composition of embodiment 1, wherein the spore-forming strain of the genus *Bacillus* is *Bacillus amyloliquefaciens* or a *Bacillus* species comprising a 16S rDNA sequence comprising SEQ ID NO:2 or comprising a 16S rDNA sequence having at least about 90%, 91%, 92%, 93%, 94%, 95%, 96%, 97%, 98%, or 99% sequence identity to SEQ ID NO:2.

Embodiment 4. The composition of embodiment 1, wherein the spore-forming strain of the genus *Bacillus* is a *Bacillus* species comprising a 16S rDNA sequence comprising SEQ ID NO:3 or comprising a 16S rDNA sequence having at least about 90%, 91%, 92%, 93%, 94%, 95%, 96%, 97%, 98%, or 99% sequence identity to SEQ ID NO:3.

Embodiment 5. The composition of embodiment 1, wherein the spore-forming strain of the genus *Bacillus* is a strain selected from a group consisting of AB01, AP79, AP143, AP193L, AP254L, deposited at the United Stated Department of Agriculture on Apr. 27, 2012, under accession numbers NRRL B-50745, NRRL B-50741, NRRL B-50742, NRRL B-50743, and NRRL B-50744, respectively.

Embodiment 6. The composition of any of the foregoing embodiments, wherein the feed composition is a feed composition for aquatic animals such as farmed fish (e.g. catfish or tilapia) and crustaceans (e.g., shrimp).

Embodiment 7. The composition of any of the foregoing embodiments, wherein the spore-forming strain of the genus *Bacillus* is present in the composition at a concentration of at least about $10^4$ CFU/g of feed.

Embodiment 8. The composition of any of the foregoing embodiments, wherein the spore-forming strain of the genus *Bacillus* is present in the composition at a concentration of at least about $10^5$ CFU/g of feed.

Embodiment 8. The composition of any of the foregoing embodiments, wherein the spore-forming strain of the genus *Bacillus* is present in the composition at a concentration of at least about $10^6$ CFU/g of feed.

Embodiment 10. The composition of any of the foregoing embodiments, comprising a single strain of the genus *Bacillus*.

Embodiment 11. The composition of any of the foregoing embodiments, comprising a mixture of strains of the genus *Bacillus*.

Embodiment 12. The composition of any of the foregoing embodiments, wherein the spore-forming strain of the genus *Bacillus* inhibits the growth of one or more bacteria selected from a group consisting of *Aeromonas hydrophila*, *Edwardsiella ictaluri*, *Edwardsiella tarda*, *Flavobacterium columnare*, *Streptococcus iniae*, and *Yersinia ruckeri*.

Embodiment 13. The composition of any of the foregoing embodiments, wherein the spore-forming strain of the genus *Bacillus* inhibits the growth of the oomycete fungus *Saprolegnia*.

Embodiment 14. The composition of any of the foregoing embodiments, further comprising a bacteriophage that infects *E. ictaluri*.

Embodiment 15. The composition of embodiment 14, wherein the bacteriophage is φeiAU.

Embodiment 16. The composition of any of the foregoing embodiments, further comprising an agent selected from a group consisting of sulfadimethoxine, ormetoprim, and florfenical.

Embodiment 17. The composition of any of the foregoing embodiments, further comprising an attenuated strain of *E. ictaluri*.

Embodiment 18. The composition of any of the foregoing embodiments, wherein the spore-forming strain of the genus *Bacillus* is susceptible to one or more antibiotics selected from a group consisting of carbenicillin, ampicillin, spectinomycin, oxacillin, vancomycin, cephalothin, novobiocin, sulfadiazine, amikacin, erythromycin, neomycin, penicillin, chloramphenicol, sulfamethoxazole, norfloxacin, gentamicin and ciprofloxacin.

Embodiment 19. A method for treating or preventing disease in an animal comprising administering the feed composition of any of the foregoing embodiments to the animal.

Embodiment 20. The method of embodiment 19, wherein the animal is an aquatic animal such as farmed fish (e.g. catfish or tilapia) and crustaceans (e.g., shrimp).

Embodiment 21. The method of embodiment 19 or 20, wherein the disease is enteric septicemia.

Embodiment 22. A microbiocidal composition formulated for administering to an aquatic environment and comprising an effective amount of a spore-forming strain of the genus *Bacillus* for treating or preventing enteric septicemia.

Embodiment 23. The composition of embodiment 22, wherein the aquatic environment is an environment where aquatic animals such as farmed fish (e.g. catfish or tilapia) and crustaceans (e.g., shrimp) are raised.

Embodiment 24. A method of treating or preventing enteric septicemia in aquatic animals such as farmed fish (e.g. catfish or tilapia) and crustaceans (e.g., shrimp) comprising administering the composition of embodiment 22 to the environment where the aquatic animals such as farmed fish (e.g. catfish or tilapia) and crustaceans (e.g., shrimp) are raised.

EXAMPLES

The following examples are illustrative and are not intended to limit the claimed subject matter.

Example 1

Biological Control of Channel Catfish Disease

Introduction

Proposed is research that has great potential to improve the environmental sustainability and economic viability of commercial production of channel catfish (*Ictalurus punctalus*) in the Southeastern United States. Enteric septicemia of catfish (ESC), caused by *Edwardsiella ictaluri*, and other bacterial and fungal pathogens (e.g., *Aeromonas hydrophila*, *Flavobacterium columnare*, and *Saprolegnia* spp.) are responsible for millions of dollars of losses to the catfish industry annually. For the aquaculture producer, the use of beneficial microorganisms for biological control of disease has the expected advantages of 1) low application costs, 2) no detrimental impact on other bacteria, the environment, or human consumers, and 3) expected synergy between biological control and existing disease control strategies.

This research will ultimately benefit catfish producers by providing them an alternative strategy to control pathogens that affect catfish, thus facilitating more efficient production and making a positive impact on the economic lives of aquaculture farmers in rural southeastern states. Furthermore, by decreasing or eliminating the need for antibiotic (or other chemical) treatment of aquaculture ponds, biological control may lessen the adverse environmental impacts of aquaculture production. Environmentally friendly and cost-effective technology with the ultimate objective of applying biological control agents to decrease the incidence and severity of disease in aquaculture ponds is desirable.

The culture of channel catfish has been one of the most successful animal production industries in North America in the past 30 years, and currently represents the largest aquaculture industry in the United States. In 2009, more than 210 million kg of catfish were processed representing over $360 million in gross farmgate sales. Over 90% of all catfish are produced in Alabama, Arkansas, Louisiana, and Mississippi and are primarily grown in earthen ponds ranging in size from 2 to 10 ha (USDA, Part I: Reference of Fingerling Catfish Health and Production Practices in the United States, 2003; USDA, Part II: Reference of Foodsize Catfish Health and Production Practices in the United States, 2003). Catfish farmers typically stock fish at high densities and use culture systems where environmental conditions can change very rapidly. These adverse conditions place added stress on the fish, creating favorable conditions for the onset and spread of different catfish diseases. As a result many diseases have emerged and become endemic in the catfish industry. The most important of these endemic infectious diseases is ESC, resulting in losses in over 78% of all operations with outbreaks being reported in 42% of foodfish production ponds (USDA, Part I: Reference of Fingerling Catfish Health and Production Practices in the United States, 2003; USDA, Part II: Reference of Foodsize Catfish Health and Production Practices in the United States, 2003). The combination of increased feed prices and high disease incidence is resulting in economic hardship for channel catfish producers.

*E. ictaluri* is a rod-shaped, Gram-negative bacterium that is highly host-specific for channel catfish (Plumb, 1999). The economic impact of this bacterium in the catfish industry has dramatically risen since first described as the causal agent of ESC in 1981 (Hawke et al., 1981). Today, it is estimated that ESC costs the catfish industry between $20 and $30 million yearly in direct fish losses (Delbos et al., 2001). Enteric septicemia occurs in acute, sub-acute, and chronic forms in channel catfish (Hawke et al., 1981). Fish with ESC are listless and often swim in slow, erratic spirals at the surface of the water. As the disease progresses hemorrhages and ulcers appear along the flanks and back of the fish. In chronically ill fish, an open lesion may develop on the top of the head, giving the disease its common name, 'hole-in-the-head disease'.

*A. hydrophila* is also a Gram-negative bacterial pathogen, which has a broader host range than *E. ictaluri* by causing a hemorrhagic septicemia in all freshwater fish worldwide (Cipriano et al., 1984; Ford et al., 1991). Losses due to *A. hydrophila* infections are typically of a much smaller magnitude than those due to *E. ictaluri* and it is often considered a secondary pathogen associated with stress, handling or opportunistic infection (Plumb, 1999); however, a 2009 epidemic of *A. hydrophila* infections among Alabama catfish producers has been unparalleled in its virulence and rapid dissemination among catfish Biological control of channel catfish disease ponds (Terhune, Liles, et al., manuscript in preparation). Outbreaks of this new *A. hydrophila* strain have been documented on 48 farms in West Alabama and caused an estimated loss of 3.8 million pounds of fish, primarily harvestable size animals where production costs inputs have already largely been made (W. Hemstreet, personal communication, Alabama Fish Farming Center, Greensboro, Ala.).

Young-of-the-year catfish are most susceptible to ESC and other pathogens. Outbreaks on fingerling operations generally begin in late August or September when the water temperatures decrease from peak summer temperatures to a range conducive for *E. ictaluri* growth (22-28° C.). Once fish have survived an initial infection, fish can become immune to subsequent infections due to response by the acquired immune system (Klesius, 1992). Usually ponds managed for the production of food-size fish are restocked with fingerlings multiple times during a production cycle to allow for continuous harvesting of the ponds. Hence, foodfish production ponds usually contain a mix of fish with different ages and immune status. Most of the adult fish in a foodfish pond have already experienced a disease outbreak and are immune to the disease but a proportion of them will be carriers of the agent (Klesius, P. H. 1992). Therefore, when naïve fingerlings are stocked in foodfish ponds they are exposed to the agent in the pond environment making them more prone to disease outbreaks (Wise et al., 1998).

Initial efforts to control ESC, *A. hydrophila*, and other bacterial pathogens were based on feeding antibiotic medicated feed. For the last 20 years, the only antibiotics labeled by the U.S. Food and Drug Administration (FDA) for controlling ESC and *Aeromonas* infections were Romet® (ormethoprim-sulfamethoxine) and Terramycin® (oxytetracycline), respectively. The FDA recently approved the use of Aquaflor® (florfenical) for ESC outbreaks and it is currently being marketed by the Schering Plough Corp. (Gaunt et al., 2003; Gaunt et al., 2004). However, medicated feed is expensive and usually marginally effective in commercial practice since sick fish may not eat adequate amounts of the medicated feed to clear the infection from the treated population. Additionally, Aquaflor may only be administered with a veterinary feed directive that requires bacterial identification and issuance by a licensed veterinarian that may further delay implementation of corrective treatment actions. The systematic use of antibiotics has also led to the development of bacterial resistance (Khoo, 2001). Recent surveys of catfish ponds in Stoneville, Miss. have shown the presence of a plasmid in *E. ictaluri* disease isolates that confers resistance to Aquaflor®24.

Most producers have incorporated the use of restricted feeding practices during ESC outbreaks to reduce mortality. However, by reducing feed inputs the growth of fish is sacrificed, severely affecting producers' profits (Wise et al., 1998). Recently, a live, attenuated strain of *E. ictaluri* has been developed for vaccination purposes and shown limited protection in fingerling channel catfish when vaccinated at 10 days of age, both under experimental and commercial conditions (Lim et al., 2003; Shoemaker et al., 1999; Wise et al., 1998; Wise et al., 2001). However, the vaccine has not been widely accepted by catfish producers since disease often occurs in vaccinated fish populations and the up-front cost can be prohibitive.

With various control strategies in use for catfish disease prevention and yet significant losses still occurring due to pathogens, other complementary approaches may be welcomed by catfish producers. An effective biological control agent would require good efficacy, be very low cost, have potent antibacterial activity, have no adverse environmental impacts, and ideally would enable marketing of catfish as an organically grown product. Biological control agents have recently been identified by the present inventors.

Rationale and Significance

Every animal is a host for a complex microbial ecosystem, with many unique microbial habitats on and within each animal. This complex microbial community can provide protection against disease and aid in the acquisition of essential nutrients. Beneficial microorganisms are being exploited as inoculants in both agriculture and aquaculture, to inhibit pathogens and enhance the health and growth of animal and plant crops. This proposed research will develop *Bacillus* strains for use in aquaculture, to 1) prevent disease due to bacterial and fungal pathogens, 2) promote sustainable aquaculture practices, and 3) benefit the economic livelihood of aquaculture producers in the State of Alabama.

The use of biological control to prevent and control diseases afflicting agriculture has already been proven to reduce the need for chemical pesticides and antibiotics in food crop production (Kloepper et al., 2004; Lewis et al., 1997; Zehnder et al., 2001). The worldwide use of the insecticidal toxin of *Bacillus thuringiensis* (Bt) as an alternative to pesticides is one example of the ability of beneficial microorganisms and their natural products to benefit food safety, reduce the reliance on chemical treatment regimes, and foster economically and environmentally sustainable production (Sanchis, 2008). As with agriculture, aquaculture relies upon high density monocrop systems, providing ideal conditions for the growth of pathogenic microorganisms. Antibiotic treatment of farm raised fish and crustaceans leads to an increasing frequency of antibiotic resistant pathogens that can be introduced into human populations, and decreases the market value for farmers forced to depend upon costly chemical methods of disease control. As the demand for quality animal protein sources increases in the 21st century, with probable depletion of wild fish stocks, there is a societal need for environmentally sustainable and cost-effective methods that can be incorporated into aquaculture farming practices (Harlander, 2002; Serageldin, 1999).

Figure 2:
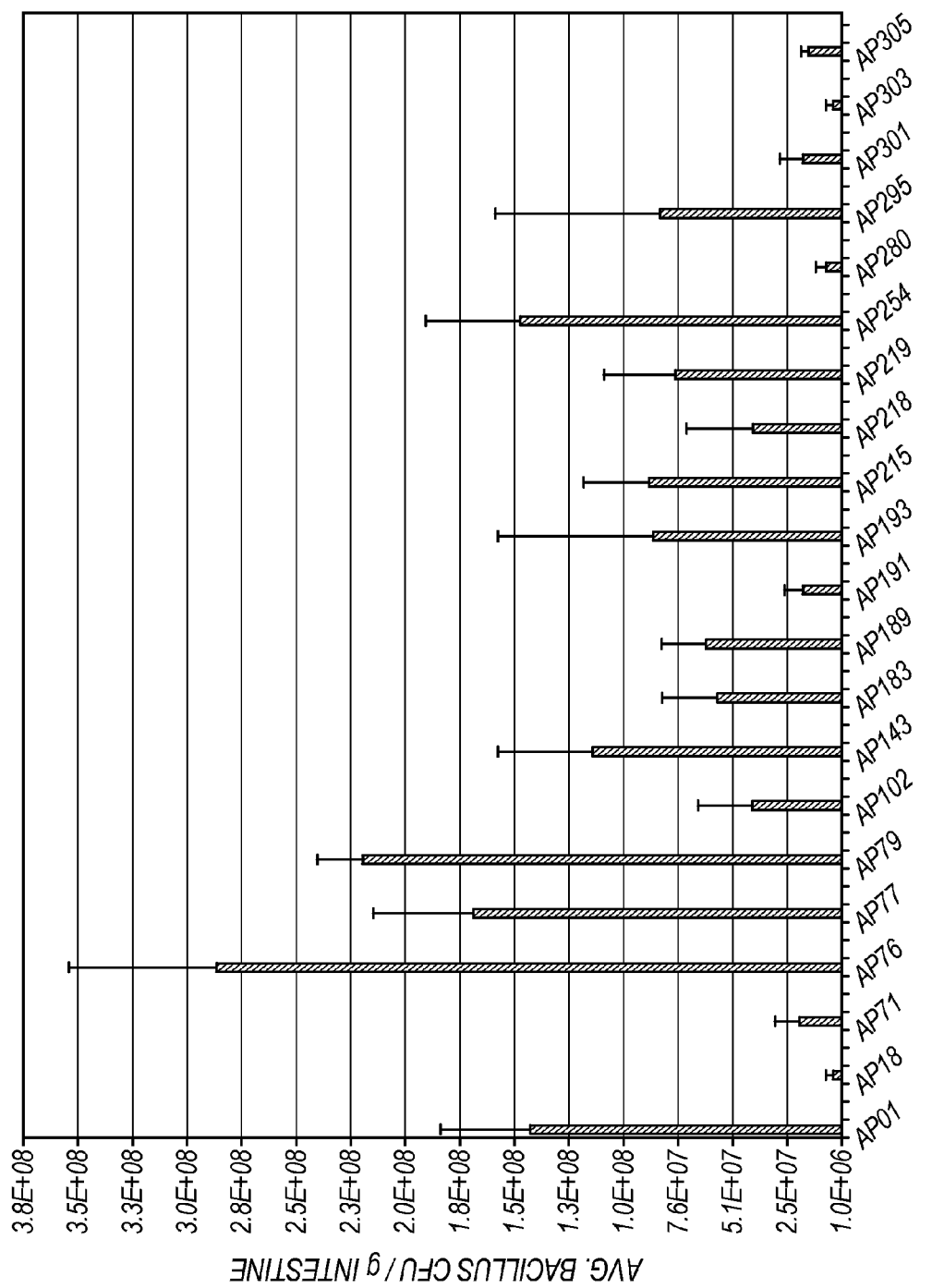
FIG. 2. illustrates *Bacillus* strain CFUs/g of catfish intestine, after feeding with *Bacillus*-amended or non-amended feed (n=3 animals per *Bacillus* strain).

The present inventors have demonstrated the efficacy of beneficial bacteria, spore-forming members of the genus *Bacillus*, to act as biological control agents in preventing disease in plants due to bacterial or fungal pathogens (Kloepper et al., "Theory and applications of rhizobacteria for transplant production and yield enhancement", 2004; Kloepper et al., "Induced systemic resistance and promotion of plant growth by *Bacillus* spp.", 2004; Kokalis-Burelle et al., 2003). In some cases *Bacillus* strains have also been found to dramatically promote the growth of crop plants and increase plant uptake of soil nutrients (Enebak et al., 1998; Kloepper et al., 2004; Kokalis-Burelle et al., 2003). Spores of *Bacillus* can be applied to the seeds or roots of plants resulting in a significant decrease in disease symptoms and mortality when the plant is exposed to a pathogen. An extensive collection of *Bacillus* biocontrol strains useful against plant pathogens (n=160), along with *Bacillus* cultures isolated from channel catfish intestinal homogenates (n=17), were tested for biocontrol activity against a panel of seven pathogens that are the major causes of aquaculture disease and economic losses worldwide (e.g., FIG. 1). Specifically, each of the bacterial isolates was tested for activity against the bacterial pathogens *A. hydrophila, E. ictaluri, E. tarda, F. columnare, Streptococcus iniae, F. columnare, Vibrio harveyi, Yersinia ruckeri*, and the oomycete fungus *Saprolegnia*. Out of this collection of *Bacillus* strains, the most effective strains for aquaculture use (n=21) have been identified based on their in vitro inhibition of pathogen growth. These 21 *Bacillus* strains were tested for their ability to survive and grow within the intestine of a channel catfish, by spraying *Bacillus* spores separately onto catfish feed (~$10^6$ CFU/g feed), feeding aquaria housed catfish fingerlings with the *Bacillus*-amended feed for one week, then feeding with regular feed for three days, and then sacrificing the animals and estimating the numbers of *Bacillus* per g of intestinal tissue (FIG. 2). Many of the *Bacillus* strains achieved high numbers (>$10^8$ CFU/g intestine) suggesting that they had successfully colonized the catfish GI tract, whereas seven strains had levels of *Bacillus* similar to the control group (from indigenous intestinal populations). Ongoing tests will determine the 16S rRNA gene sequences of representative *Bacillus* colonies recovered from the catfish intestine, to verify that these were the same strains that were introduced to the animals on amended feed.

Figure 3:
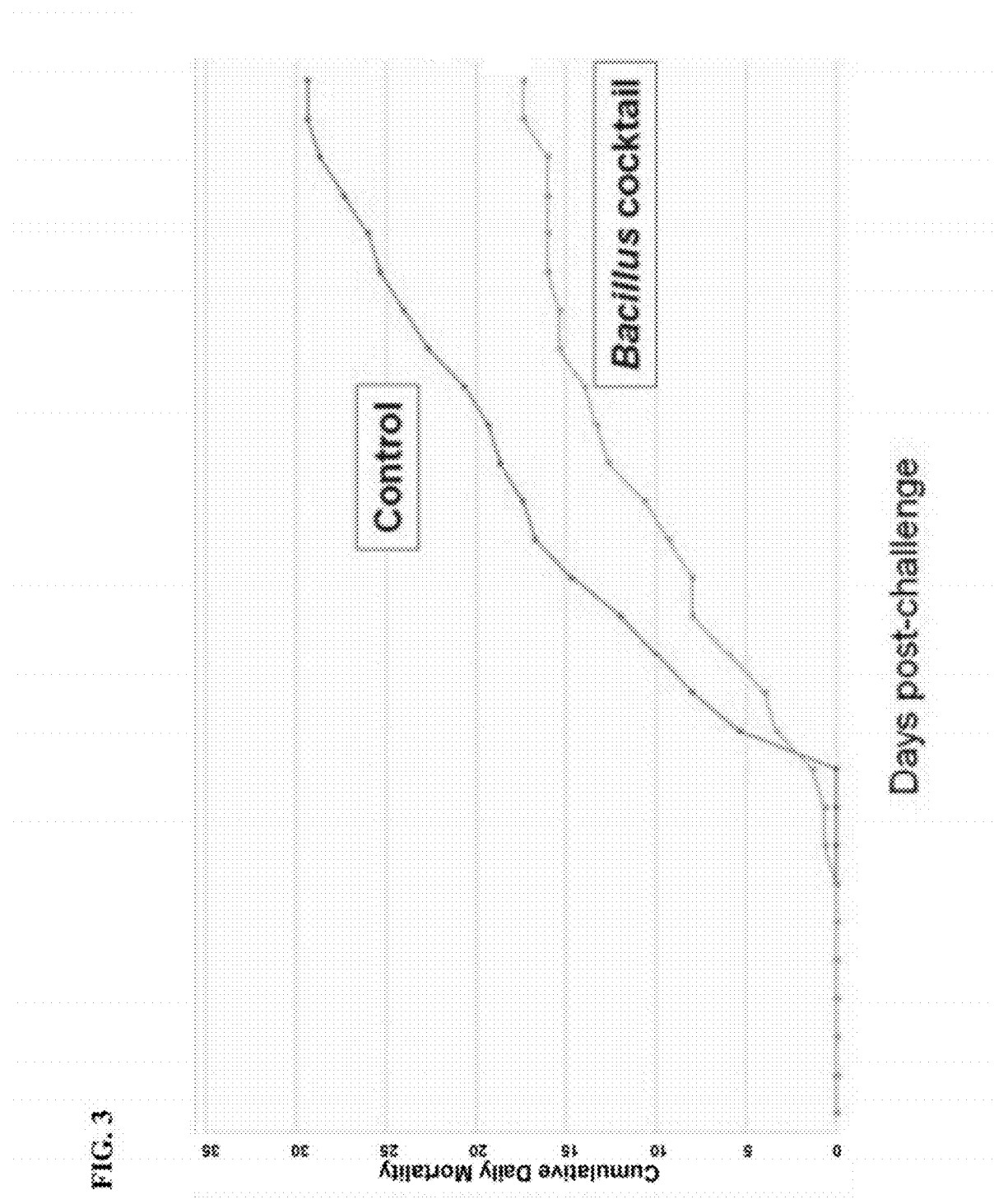
FIG. 3 illustrates cumulative daily mortality of channel catfish fingerlings exposed to ESC with and without being feed *Bacillus*-amended feed.

A "*Bacillus* cocktail" was prepared by selecting several *Bacillus* strains and applying *Bacillus* spores onto catfish feed at approximately equal $10^5$ CFU per strain/g feed. The *Bacillus*-amended feed was fed to fingerling catfish (n=15 per tank, 5 tanks per treatment group) for two days prior to immersion challenge with $2 \times 10^5$ CFU/ml *E. ictaluri* strain S97, and then mortalities were recorded over time. A significant decrease in mortality was observed for the catfish fed the *Bacillus* amended feed, relative to the control group (FIG. 3). This experiment demonstrated that *Bacillus* spores introduced onto the feed of channel catfish have the ability to reduce disease and mortality in a controlled aquarium model of disease. Together in this proposal these scientists will test *Bacillus* biocontrol strains for disease control in channel catfish, conducting the critical experiments to develop these *Bacillus* strain(s) for biological control application.

Despite the promise of probiotic, beneficial microorganisms for disease control, this field of science has been limited by a lack of scientific rigor in evaluating some proposed probiotics, and a need to systematically evaluate many possible biological agents for those that can both be effective and gain regulatory approval. The experiments disclosed herein will 1) identify specific *Bacillus* strains that may be used for disease control through application onto channel catfish feed, 2) complete a genome sequence for the specific *Bacillus* strain(s) that show the best promise in disease prevention, 3) determine the structure of the antibiotic(s) produced by each *Bacillus* strain, 4) perform efficacy studies on the ideal dose and timing for *Bacillus* administration, and 5) evaluate catfish health after long-term feeding with *Bacillus* amended catfish feed. For this study, the *Bacillus* strains are being selected through rational evaluation of their relative efficacy in disease prevention, and for the specific criteria above that are important for their successful use for channel catfish production.

Approach

Testing of the Relative Benefit of Each *Bacillus* Strain for Control of ESC.

Controlled experimental infections in aquaria will be used to assess bacterial biological control for each specific bacterial strain. Several variables will be assessed in establishing the protective effect of bacterial cultures for their respective biological control activity. Since long term ambient storage may be a requirement for commercial application, endospore forming bacteria within the genus *Bacillus* have been selected for evaluation for their biological control potential. Of the 15 *Bacillus* cultures that 1) express robust inhibitory activity against multiple aquaculture pathogens (e.g., FIG. 1), and 2) can survive and replicate within the catfish intestine (FIG. 2), these will be screened separately to identify the most effective strains for in vivo protective effect against ESC in aquaria challenges. Each *Bacillus* culture will be grown on a sporulation medium for 48 hours and then bacterial cells will be removed with a sterile cotton swab and suspended in sterile water within a 50 ml conical tube. After washing twice with sterile water, the spore suspension will be tested for viable colony forming units (CFUs), and then used to coat catfish feed with approximately $10^7$ bacterial CFU/g feed by spraying a spore suspension at a dose of 8% (v/w). The bacteria coated feed will be dried prior to feeding the catfish. *Bacillus* spore-coated feed will be stored at 4° C. prior to feeding and is anticipated to be highly stable for long-term (months) storage due to endospore formation.

Assessment of Individual *Bacillus* Strains to Prevent ESC in Controlled Aquarium challenge.

In these challenge experiments, four aquaria per *Bacillus* strain, or control group, with 15 fingerling specific-pathogen-free catfish per aquarium will be used. One week prior to challenge, catfish feed coated with specific *Bacillus* strains will be fed to the fingerling catfish to satiation one time per day, with control tanks receiving sterilized bacterial cells (by autoclaving), or no bacterial addition. For the challenge assay, log-phase *E. ictaluri* cultures at approximately $10^5$ CFU per ml will be added to the aquaria under static conditions. Fish survival will be monitored daily with end survival rates in each of the treatments used to assess the ability of each *Bacillus* strain to prevent development of ESC. Control tanks will receive viable bacteria amended feed but will not receive *E. ictaluri* to verify that there is no detrimental effect of the *Bacillus* on catfish viability.

Characterize the Antibiotic Compound(s) Produced by Each *Bacillus* Strain.

Each of the antibiotic-producing *Bacillus* strains has been found to secrete an inhibitory compound(s) into their growth medium. Cell-free supernatants of *Bacillus* strains grown either in an M9 minimal medium, or in a complex tryptic soy broth medium, have antibiotic activity against the pathogens previously tested in a cell-based bioassay (e.g., FIG. 1). Identification of the antibiotic compound(s) produced by *Bacillus* strains will be very important for eventual regulatory approval for use of these strains, either solely or in combination, for disease control.

Partially Purify the Antibiotic by Liquid Chromatography (LC).

The compounds will initially be purified using size exclusion and reverse phase LC and tested utilizing the bioassays disclosed herein. The partially purified compounds will be exposed to different organic extraction and phase separations to determine conditions for rapid extraction from spent media. After defining these conditions, the purification will proceed using the defined C18 retention index as a 'final' purification step. The strategies will endeavor to achieve rapid purification of the bioactive compound, restricting the purification to a three-stage protocol when possible.

Many drug synthesis pathways produce more than one product. In addition to inactive compounds, these can include chemically related antibiotics with varying potencies and spectra of activities. For instance, the bacterium that produces epothilone, a candidate anticancer agent, secretes chemically similar epothilones A, B, and D into its medium (Tang et al. 2000). Co-occurring drug-like molecules such as these can be separated by LC as multiple peaks of activity among the fractions. The initial LC partial purification step will separate active compounds and characterize each individual compound's spectrum of antibiotic activity. Purification of individual components to homogeneity will greatly enhance the prospect of successful downstream mass spectroscopy (MS) analyses.

Three types of antibiotic molecules might be obtained: small peptides, organic molecules, or lipids. Size exclusion and C18 chromatography will be able to separate these classes. Failure to be retained on C18 may necessitate additional chemistries be attempted; however, in initial screens of *Bacillus* antibiotics, we will favor those UV-active compounds that appear to be monodisperse in initial purifications. Variation in the solvent systems and pH will be used to enhance the separation of complex mixtures, while the bioassays disclosed herein provide a powerful tool to monitor integrity of our molecules. The active compounds that can be purified in quantities will be analyzed for structural information by LC/MS. Many potential hurdles can impede compound purification. Some biological activities are due to multi-subunit molecules, which may lose activity when the components are separated by chromatography (e.g., violacein). Additionally, solvation and other treatments during LC may inactivate some molecules. To discern between these two options, different chromatography fractions can be combined and tested for the return of activity.

Chemical Characterization of the Active Compounds.

Chemical characterization of the active compounds will be attempted using thin layer chromatography and MS analysis. Thin layer chromatography (TLC) will be used as an inexpensive strategy to study the homogeneity of the final compound (e.g., monitoring with UV, sulfuric acid charring) and the chemical functionalities (e.g., Ninhydrin reactivity or acetylation reactions) for the antibiotics produced by *Bacillus* strains. These initial chemical assays will lay the foundation for complex analysis such as MS and NMR. The LC/MS conditions will also permit circumvention of any potential ion suppression that may be present in the mixed samples. Further LC/MS experiments will also be valuable in the refinement of the purification strategies. Additional LC/MS/MS and accurate mass experiments will be performed to sort compounds into groups with structural similarities. Structural data from a single round of LC/MS/MS is often insufficient to completely determine molecular structures. Nonetheless, the data can be matched to literature values to identify previously described compounds. Even incomplete structural data can be used to predict solubility and stability, and determination of molecular weights enables production of solutions at known molar concentrations. The ability to prepare known concentrations of antibiotic compounds is important for determining potency and cytotoxicity. Chemical structure analyses will be performed. Preliminary LC/MS data will aid in the active molecule structural determination. Extraction and chemical analysis to discover structures of the product molecules are relatively expensive processes. To conserve the project budget, complete chemical structure analyses will be performed only for a small number (e.g., <6) of highly active antibiotic compounds that have passed the previous evaluations, and corresponding to *Bacillus* strains identified as having significant biological control activity. Promising candidate molecules from each structural similarity group will be further characterized using the full set of spectroscopic techniques (UV-vis, UV-vis-NIR, FT-IR, FT-Raman, GC-FTIR, resonance Raman, and NMR spectroscopy). In the initial phase, one-dimensional $^1$H and $^{13}$C NMR (at natural abundance) experiments and multi-dimensional NMR $^1$H-$^{13}$C (at natural abundance) Heteronuclear Single Quantum Coherence (HSQC) experiments will be performed to categorize compounds. Full NMR analyses may also be performed.

Determined Relative Potency of Antibiotic Compounds Against Different Pathogens.

Absolute and relative potency data may be utilized to rank compounds for their potential as antibiotics. Each of the bacterial and fungal pathogens tested previously (n=7, see above) will be exposed to dilution series of purified antibiotic compound(s) to determine Minimum Inhibitory Concentrations (MICs). Purified compounds and molecular weight data from LC/MS structural analyses will be used to dissolve compounds to known concentrations. Standard antibiotic assay conditions and media (cation-adjusted Mueller-Hinton broth, when appropriate) will be employed to assess antibiotic potency. Briefly, bacterial cultures in the log phase of growth will be inoculated with a wide range of antibiotic concentrations, in triplicate, and growth inhibition will be determined relative to the negative control (solvent or buffer used for antibiotic compound). Growth kinetics will be determined for each bacterial species for calculation of $MIC_{50}$ (50% growth inhibition), and the potency of each compound will be compared relative to other known antibiotic compounds. Positive controls will include antibiotics of different classes with previously defined potencies.

Sequence the Genome of the Most Effective *Bacillus* Biocontrol Strain(s).

The *Bacillus* strains identified by the experiments herein may be sequenced. The DNA sequence information obtained may be utilized to begin DNA-based strain-specific tracking systems for monitoring the movement of introduced beneficial strains in the environment. In addition, this work will provide an extensive genetic inventory of the biosynthetic pathways involved in natural product synthesis and indicate the metabolic and enzymatic capabilities of each strain, enabling future work to use these genome sequences to assay for *Bacillus* global gene expression and to enhance antimicrobial biosynthesis during biological control.

Genome Sequencing and Assembly of a *Bacillus* Strain.

The genome size of each prospective *Bacillus* strain will be estimated by pulsed field gel electrophoresis (PFGE). Most *Bacillus* genomes are 4 to 7 Mbp, so using a next-generation sequencing approach can easily generate 50× fold coverage of a *Bacillus* genome. A combined approach using both 454 pyrosequencing for >30× genome sequencing coverage (~500 bp read lengths), and >50× genome sequencing coverage using illumina sequencing (~70 bp paired end read lengths) is an optimal strategy for de novo bacterial genome sequencing. *Bacillus* cultures will be grown in large scale (500 ml) for DNA extraction, and the genomic DNA will be prepared as a barcoded sublibrary and sequenced. By using a ½ plate 454 format, a sufficient degree of sequencing coverage should be obtained for a single *Bacillus* genome. The genome sequences will be assembled into a contiguous genome. A bioinformatics software package, CLC Bio Genome Workbench will be utilized to perform high-throughput de novo genome assembly and annotation. In particular, the genome analysis will attempt to identify genetic pathways involved in antibiotic synthesis, and scanning the genome for evidence of any gene(s) potentially involved in pathogenesis (e.g., hemolysins, toxins). A list of predicted open reading frames (ORFs) will be identified using a hidden markov model trained on other completely sequenced *Bacillus* genomes. The database of *Bacillus* ORFs will be compared to the GenBank nr/nt database by BLAST algorithm searches, and a preliminary annotation prepared according to the top GenBank hit for each respective ORF. The complete (or nearly complete) *Bacillus* genome will be a valuable resource for future gene mining and gene expression experiments to support extramural funding opportunities.

Generation of *Bacillus* Mutants that Lack Antibiotic Synthesis.

To identify the specific gene(s) required for antibiotic synthesis, a Mariner transposon system (Wilson et al., 2007) will be used to randomly transposon mutagenize the *Bacillus* strains (n=3) that will be selected for complete genome sequencing. The *Bacillus* Tn mutants will encode spectinomycin resistance, and each mutant colony will be overlayed with soft agar (0.7%) containing a log phase culture of *E. ictaluri*. Each of the mutants that lack a zone of inhibition will be selected for further study. It will be possible to very rapidly screen tens of thousands of mutants for loss-of-function in this manner, providing an exhaustive collection of antibiotic-deficient mutants. Each of the mutants will be compared by Southern blot analysis using a probe targeting the transposon cassette, thereby indicating mutants with a transposon insertion in the same (or immediately adjacent) genetic locus. Every unique mutant will be tested against a wider panel of bacterial and fungal pathogens described above, to determine if the loss-of-function for an antibiotic that inhibits *E. ictaluri* growth is similarly lacking for the other pathogens. It may be the case that a *Bacillus* strain could express multiple antibiotics, in which case different pathogens may be used for the primary screen in order to identify a loss-of-function mutant deficient in antibiotic synthesis.

To identify the gene(s) required for antibiotic synthesis, the genomic DNA of unique mutants will be extracted and used as template for inverse PCR using primers internal to the transposon cassette to identify the *Bacillus* gene(s) adjacent to the site of transposon insertion. The DNA sequences will be compared to the complete *Bacillus* genome sequence (as the reference genome) to indicate the relative location of each transposon insertion within the genome. This will be critical information to understand the genetic pathway(s) involved in synthesis of an antibiotic that can impair the growth or viability of *E. ictaluri* and other pathogens. By using multiple *Bacillus* strains for biological control, this is in effect using a multi-drug formulation, thereby reducing the likelihood of drug-resistant pathogens. It would also be of interest to test whether a *Bacillus* mutant lacking antibiotic synthesis would be impaired in its biological control activity, compared to its wild-type parent strain.

Develop the Optimal Formulation of *Bacillus* Strains for Biological Control of Disease.

The choice of the optimal *Bacillus* strain, or combination of strains, for biological control of disease may be informed by many different sources of experimental data. This proposed research will identify the optimal *Bacillus* strain(s) and conditions of for control of ESC.

*Bacillus* Dose-Dependence.

In the first of these experiments to evaluate each strains' ability to control disease in vivo, four of the best *Bacillus* strains identified above as preventing *E. ictaluri* infection and mortality will be used to determine the best dose to incorporate into feed for administration. *Bacillus* spores and feed preparation will be performed as described above; however, the number of spores incorporated into the feed will be altered. The doses will comprise $10^4$, $10^5$, $10^6$, or $10^7$ CFU/g of feed plus a control treatment. Fish will be placed into challenge aquaria (as described above) divided into treatments (with five replicate aquaria per dose) and fed treatment feed daily to satiation, with feeding of the treated feed continuing for 2 weeks. Fish will be challenged under static immersion as described above. Fish will not be fed on the day of challenge, but will resume feeding one day post-challenge and continue throughout the challenge study with the assigned treatment feed. Mortalities will be monitored for at least 21 days. Each *Bacillus* strain will be evaluated separately.

*Bacillus* as a Prophylaxis or a Cure.

In a second series of experiments, *Bacillus* strains will be tested with respect to prophylactic and/or ability to eliminate ongoing infections. These tests will be performed via altering the time at which the spores are initially fed to fish in relation to the timing of challenge. For each *Bacillus* strain identified and utilized above, four initiating times will be evaluated plus a control group. Fish will be stocked into challenge aquaria as described above and randomly assigned into one of five treatments: 1) *Bacillus*-amended feed started 1 week prior to challenge, 2) *Bacillus*-amended feed started 3 days prior to challenge, 3) *Bacillus*-amended feed initiated 1 day post-challenge, 4) *Bacillus* amended feed initiated the day of the first *E. ictaluri* related mortality (based on clinical and behavioral signs), and 5) control feed. All treatment groups will be fed *Bacillus*-amended feed throughout the experiment with feed amount being offered to satiation. Feed preparation and challenge protocols will be conducted as described above.

Growth and Pathology Related to *Bacillus* Administration.

Based on the dose of *Bacillus* identified above, catfish will be subjected to a growth performance trial with each of the four best identified bacterial strains and their respective best dose. Feed will be prepared as previously described with the appropriate *Bacillus* dose. Juvenile fish (~5 g each) will be counted, weighed collectively, and placed into aquaria and randomly assigned the designated feed treatment with four replicate aquaria per treatment, 16 fish per replicate tank. Fish will be fed one time daily with approximately 4-5% body weight (approximate satiation; based on initial weight) with prepared feed. Feed will be weighed daily. Every two weeks for eight weeks, all fish will be removed from the tank weighed collectively and weight used to adjust amount of feed offered. At weeks four and eight, four fish from each tank will be removed from each tank. A section of the lower intestine will removed and used to assess the number of desired *Bacillus* organisms (CFU/g) inhabiting the tissue. The remaining fish tissues will be preserved in 10% neutral buffered formalin for histopathological evaluations. Final weights of the fish will be used to determine growth performance impacts and feed conversion rates.

Combinations of Different *Bacillus* Strains ("Cocktails") for ESC Biological Control.

Use each *Bacillus* strain, at its ideal dose, in every possible combination to assess each *Bacillus* "cocktail" for its potential in controlling ESC disease. Treatment feeds will be prepared as previously described with equal spore doses of one to four *Bacillus* strains. Fish challenge experiments will be conducted as described above, utilizing five replicate aquaria per cocktail treatment with 15 fish per replicate. Fish will then be fed the appropriate treatment feed for one week prior to challenge and then continuously post-challenge for the duration of the experiment.

Example 2

Identification of *Bacillus* Strains for Biological Control of Catfish Pathogens In the following Example 2, research proposed and completed in Example 1 was further performed and replicated.

Abstract

*Bacillus* strains were selected and evaluated for biological control of disease in catfish. *Bacillus* strains were isolated from soil or channel catfish intestine and screened for their potent antagonism against *Edwardsiella ictaluri* and *Aeromonas hydrophila*. Twenty one strains were selected and their antagonistic activity against other aquatic pathogens was also tested. The survival of each *Bacillus* strain in the channel catfish intestine was determined, and five *Bacillus* strains with the best spectrum of antimicrobial activity and intestinal survival were further evaluated for their protective activity against *E. ictaluri* challenge in replicate aquaria. Two *Bacillus* strains conferred significant benefit in reducing catfish mortality ($P<0.05$). A similar challenge experiment conducted in Vietnam with four of the five *Bacillus* strains also showed protective effect against *E. ictaluri* in striped catfish. Safety study in three of the selected strains did not show presence of plasmids and resistance to clinically important antibiotics. *Bacillus* strains were beneficial to catfish when administered as a feed supplement for the control of diseases caused by *E. ictaluri*. The *Bacillus* strains selected in this study have potential application in aquaculture as a cost-effective alternative to the current use of antimicrobial compounds.

Introduction

Aquaculture farming of the channel catfish, *Ictalurus punctatus*, has been one of the most successful animal production industries in North America in the past 30 years and currently represents the largest aquaculture industry in the United States. Over 90% of all catfish produced in the U.S. are raised in Alabama, Arkansas, Louisiana, and Mississippi and are primarily grown in earthen ponds ranging in size from 2 to 10 ha (USDA 2003a, 2003b). Catfish farmers typically stock fish at high densities.

High feed inputs associated with high density fish culture stimulate the proliferation of opportunistic bacteria (Austin et al. 1995). Also, the high fish density and rapidly changing temperature and chemical composition of aquaculture ponds place stress on the fish, creating favorable conditions for the onset and spread of disease. Enteric Septicemia of Catfish (ESC), caused by the Gram negative bacterium *Edwardsiella ictaluri* (Hawke 1979), is the most important endemic infectious disease in the channel catfish aquaculture industry (Hawke and Khoo 2004). Losses resulting from ESC were reported in over 78% of all operations with outbreaks being reported in 42% of catfish production ponds, with an economic loss between $20 and $30 million yearly (Wagner et al. 2002; USDA 2003a, 2003b).

Another important pathogen in channel catfish is *Aeromonas hydrophila*, which is the primary causative agent of motile aeromonad septicaemia (MAS) (Harikrishnan et al. 2003) and can infect multiple fish species including tilapia, catfish, goldfish, common carp, and eel (Pridgeon et al. 2011). In 2009 and 2010, *A. hydrophila* was identified as the etiologic agent of a disease epidemic in farmed channel catfish, resulting in higher mortality rates than typical for MAS with over 5 million pounds of catfish lost in the Alabama commercial catfish industry. The *A. hydrophila* strains (e.g., strain AL09-119) isolated from diseased fish during this epidemic are highly virulent in aquaria disease challenge trials compared to *A. hydrophila* reference strains (Pridgeon et al. 2011).

*Pangasianodon hypophihalmus* Sauvage, commonly known as the striped catfish, is the native catfish in the Mekong Delta of Vietnam. The farming sector of *P. hypophthalmus* has recorded the highest growth rate in volume compared to any other aquaculture commodity globally over the last decade (Phan et al. 2009; Phuong and Oanh 2009). The sector accounted for 687,000 and 1,094,879 t production, in 2007 and 2008, respectively, the latter amounting to 34% of the total aquaculture production in Vietnam, the fifth-ranked nation in global aquaculture production (De Silva et al. 2010). Furthermore, over 90% of the farmed catfish is processed and exported to more than 100 countries globally (Phuong and Oanh 2009). Bacillary necrosis of *Pangasius* spp. (BNP), also caused by *E. ictaluri*, is an economically significant disease for striped catfish aquaculture industry in the Mekong Delta, which can cause 50-90% mortality and occurs in 98% of farms (Phan et al. 2009).

Chemotherapy by oral administration of antibiotics in fish feeds is the most common treatment for bacterial diseases; however, the use of antibiotics in aquaculture may introduce potential hazards to public health and to the environment by the emergence of drug-resistant microorganisms and antibiotic residues (Johnson 1991; DePaola et al. 1995; Plumb et al. 1995). Furthermore, the normal commensal microorganisms in the digestive tract, which contribute to fish health and nutrition, are inhibited by oral chemotherapy (Gerald and Jane 1966; Sugita et al. 1990). In order to rectify this situation, greater emphasis has been placed on improved husbandry through better nutrition, improved water quality, lower stocking densities, and the use of vaccines and non-specific immunostimulants (Austin and Austin 1999). Few studies have been conducted to investigate probiotic bacteria for mitigating infectious diseases in channel catfish, and no studies have been reported using direct administration in feed. Queiroz and Boyd (1998) applied a commercial probiotic product, Biostart, which contained a few species of *Bacillus* spp., to channel catfish pond water and demonstrated that survival and net production of fish treated with *Bacillus* spp. were significantly greater than the control. However, the bacteria used in this previous research were not isolated specifically for use in channel catfish nor were their antimicrobial activity against important pathogens of channel catfish characterized.

In this research an extensive collection of *Bacillus* strains (n=160) isolated from soil and strains from the intestine of channel catfish (n=17) was tested for in vitro antimicrobial activity against *E. ictaluri* strains isolated from diseased catfish, *A. hydrophila*, and other bacterial and fungal pathogens of channel catfish. *Bacillus* strains that showed effective antibiosis were evaluated for their respective survival in the intestine of channel catfish. The biological control activity of the best performing *Bacillus* strains when amended onto feed was investigated using channel and striped catfish disease challenge studies in an aquarium system. The safety of selected *Bacillus* strains was also assessed in terms of the presence of plasmids and resistance to antibiotics.

Material and Methods

Bacterial Strains.

*E. ictaluri* strain S97-773 was used for the primary screening for *Bacillus* antibiosis and for ESC challenge experiments since this strain is highly pathogenic for channel catfish and has previously been used in challenge studies at Southeastern Cooperative Fish Disease Laboratory (SCFDL), Auburn University. *E. ictaluri* strain R-4383, *E. ictaluri* strain Alg-08-200, *Edwardsiella tarda, Streptococcus iniae, Yersinia ruckeri, Flavobacterium columnare*, and *Saprolegnia ferax* were from the collection of pathogenic isolates at the SCFDL. *E. ictaluri* NLF33 were isolated from diseased striped catfish in Vietnam. *Aeromonas hydrophila* AL09-119 was isolated from a diseased channel catfish with MAS in 2009. The collection of soil-derived *Bacillus* strains (n=160) was provided by the laboratory of Dr. Joseph Kloepper (Department of Entomology and Plant Pathology, Auburn University). *Bacillus subtilis* 1E17 was obtained from *Bacillus* Genetic Stock Centre.

Isolation of *Bacillus* spp. Strains from the Intestine of Channel Catfish and Evaluation of Antimicrobial Activity.

Healthy catfish (7-10 cm) were killed by administration of an overdose of MS-222, and the digestive tracts were removed in their entirety. Approximately 1.0 g was homogenized in 9.0 ml of sterile saline (0.9% w/v). Ten-fold serial dilutions were prepared to $10^{-6}$ in fresh saline, and 0.1 ml was spread over the surface of triplicate plates of tryptone soy agar (TSA) with incubation at 28° C. for 48 h (Irianto and Austin 2002). *Bacillus*-like colonies were picked at random, purified by streaking for isolated colonies on fresh media, and examined for inhibition against the growth of *E. ictaluri* using the double-layer soft agar method (Jack et al. 1996). For the soft agar overlay, the bacterial isolates were grown in 5 ml of tryptone soy broth (TSB) for 24 h at 30° C. A volume of 5 µl was then spotted onto triplicate plates of TSA and incubated for a further 24 h. Soft agar (0.7% w/v agar) prepared with TSB was melted and cooled to 37° C. and seeded with an inoculum of log-phase *E. ictaluri* strain S97-773 to achieve slight turbidity (i.e., $10^7$ cells/ml). The bacterial cell suspension in soft agar was immediately poured over the TSA plates and incubated for 24 h at 30° C. whereupon the presence of zones of clearing in the growth of the lawn of *E. ictaluri* were recorded (in mm) as evidence of growth inhibition. Cultures that were regarded as inhibitory to *E. ictaluri* were characterized by Gram staining and 16S rRNA gene sequencing using the 'universal bacteria' primer set 27F and 1492R (Weisburg et al. 1991). A consensus 16S rRNA sequence was produced using Chromas Pro (Technelysium Pty Ltd., Queensland, Australia), and each sequence was compared to the GenBank non-redundant nucleotide database by BLASTn. *Bacillus* spp. strains were cryopreserved at −80° C. The collection of soil-derived *Bacillus* strains (n=160) was tested for antimicrobial activity against *E. ictaluri* using the same method.

Fifty *Bacillus* strains with antagonistic activity against *E. ictaluri* S97-773 were tested for their inhibitory activity against other *E. ictaluri* strains (*E. ictaluri* R-483, *E. ictaluri* Alg-08-200). *Bacillus* strains that showed antimicrobial activity against all three *E. ictaluri* strains were evaluated further for their activity to inhibit the growth of *A. hydrophila* strain AL09-119. Twenty-one *Bacillus* strains that showed significant antimicrobial activity against both *E. ictaluri* and *A. hydrophila* were tested for their activity against several other channel catfish pathogens including *Edwardsiella tarda, Streptococcus iniae, Yersinia ruckeri, Saprolegnia ferax* with the soft agar overlay method described above.

The antimicrobial activity against *Flavobacterium columnare* was tested by an agar well diffusion method. For the well diffusion assay, the *Bacillus* strains were grown in 5 ml of TSB for 48 h at 30° C. After centrifugation at 3,600×g for 10 min, the culture supernatant was filtered through a 0.2 µm filter. Then 200 µl of the filter-sterilized supernatant was added to a round well (approx. 20 mm in diameter) made in a *F. columnare* growth medium (FCGM) agar plate (Farmer 2004). After the supernatant was absorbed into the agar medium, a log-phase *F. columnare* culture grown in FCGM broth was spread thoroughly over the plate using a sterile cotton swab. The plates were incubated for 48 h at 30° C.

*Bacillus* strains AP79, AP143, AP193L, AP254L, and AB01 were also tested for their in vitro antimicrobial activity against *E. ictaluri* NLF33, the causative agent of BNP in striped catfish. A broth culture of *E. ictaluri* was adjusted to $10^6$ CFU/mL and evenly swabbed onto TSA plates. Three wells were punched from the agar plate and 50 µL of a $10^8$ CFU/mL of a *Bacillus* cell-free supernatant (48 h culture in TSB) was added into each well. Zones of inhibition were measured after 24 hours incubation at 30° C.

*Bacillus* Genome Sequencing.

*Bacillus* strain genomic DNA was extracted from 500 ml cultures grown in TSB using the Promega genomic DNA isolation kit (Madison, Wis.). The yield and purity of the genomic DNA were estimated using a Nanodrop spectrophotometer (Thermo Scientific, Wilmington, Del.), and approximately seven micrograms of *Bacillus* genomic DNA was sent to the Lucigen Corporation (Middleton, Wis.) for bar-coded sub-library generation for 454 pyrosequencing with titanium chemistry. Bar-coded *Bacillus* sub-libraries were sequenced at the Genomic Services Lab at Hudson Alpha (Huntsville, Ala.) using a Roche 454 Genome Sequencer FLX (Branford, Conn.) with either two *Bacillus* genomes per one-half 454 plate (strains AP143 and AP 254L) or three *Bacillus* genomes per a full 454 plate (strains AP18, AP193L, and another strain not described in this study). The genome sequences were imported into the CLC Genomics Workbench (Cambridge, Mass.), trimmed for quality at 0.01 stringency, and de novo assembled using assembly settings of length fraction=0.5 and similarity=0.8. The collection of contiguous genome sequences (contigs) larger than 10 kb was exported into a FASTA formatted file, and each contig was compared to the GenBank nr database by BLASTn. In addition, the open reading frames (ORFs) on each contig were predicted with the GeneMark.hmm for Prokaryotes program, which used the *B. subtilis* ORF-finding model. The predicted ORFs for each *Bacillus* genome were compared to the sequences in the nr database at GenBank by BLASTn and BLASTx. The percent identity of the *Bacillus* genome sequences to known *Bacillus* genomes in the GenBank database was estimated by including the BLAST results of all contigs greater than 10 kb together and assessing the cumulative percent identity for all contigs against specific *Bacillus* genomes for the respective aligned genome regions divided by the total number of sequenced base pairs within these contigs. In this way, the species designation for each of the sequenced *Bacillus* strains was determined and is indicated in Table 1, with % identity values of greater than 70% indicative of a species affiliation.

Preparation of *Bacillus* Spores and Spore-Amended Feed.

*Bacillus* spores were prepared by the method described by Kenny and Couch (1981) with some modifications. *Bacillus* strains were grown in TSB at 30° C. overnight. Then the broth was spread on spore preparation agar (peptone 3.3 g/l, beef extract powder 1.0 g/l, NaCl 5.0 g/l, $K_2HPO_4$ 2.0 g/l, KCl 1.0 g/l, $MgSO_4.7H_2O$ 0.25 g/l, $MnSO_4$ 0.01 g/l, lactose 5 g/l, agar 15 g/l) by a sterile cotton swab and incubated at 28° C. for 5 to 7 days. To collect the spores, 5 ml of sterile distilled water was added to the plate and the spores were suspended in water using an inoculation loop. The spore suspension was then incubated at 85° C. for 15 min to kill the vegetative cells. The concentration of the spore suspension was determined by serial dilution and spreading onto TSA. The final concentration of the spore suspension was manipulated with sterile water to $1.25 \times 10^{10}$ CFU/ml for the intestinal survival assay and $10^9$ CFU/ml for the ESC challenge study. To prepare spore-amended feed, 80 ml of the spore suspension was sprayed onto 1000 g commercially available slow-sinking pelleted fish feed (2 mm, 40% protein, Zeigler, Gardners, Pa.) using a bleach- and ethanol-sterilized pump sprayer to achieve approximately 8% v/w spore suspension application. The feed was then mixed thoroughly with 30 ml fish oil. The control feed was ammended solely with fish oil.

Inoculation and Quantification of *Bacillus* spp. in the Intestine of Channel Catfish.

Fingerling channel catfish (7-10 cm) were distributed into twenty-two 60 L tanks each containing 15 L water and three fish. Fish were starved for one week prior to the experiment. Catfish feed was amended in separate batches with the 21 *Bacillus* strains that showed good antimicrobial activity against both *E. ictaluri* and *A. hydrophila* using the spore application method described previously. Each unique *Bacillus* strain-amended feed ($\sim 10^9$ CFU/g feed) was given to one aquarium tank. The fish were fed once daily with spore-amended feed or control feed for one week, and thereafter all fish received the control feed for three days. One tank was used as the control and received untreated fish feed for the duration of the experiment. Daily feeding rate was 3% of total body weight.

At the end of the experiment, all of the fish were killed by administration of an overdose of MS-222. The intestine was removed, weighed, and then homogenized in 2 ml of sterile saline (0.9% w/v). Homogenized samples were then serially diluted in sterile saline and spread on TSA and incubated at 28° C. for 48 h. Three representative colonies with the same morphology as the applied *Bacillus* strain were randomly picked from the plate, purified on new plates and identified by 16S rRNA gene sequencing as described previously and compared with the known 16S rRNA gene sequence from each *Bacillus* strain. For the control and treatment groups, only the unique colony morphology corresponding to that of the amended *Bacillus* strains was recorded. Culturable counts for each *Bacillus* strain recovered from the intestine were determined as CFU/g of intestine sample.

Aquarium Challenge Studies.

Five *Bacillus* strains (AB01, AP143, AP193L, AP254L, and AP79) were selected for further evaluation in an aquarium challenge trial with *E. ictaluri* strain S97-773. Five *Bacillus* treatments and one control each with four replicate aquaria were included. Each replicate aquarium was stocked with 25 fingerling channel catfish weighing about 13 g. Fish were acclimated to commercial dry feed for one week. Fish from each treatment group were then fed with an experimental diet supplemented with spore of a *Bacillus* strain ($8 \times 10^7$ CFU/g) at a daily feeding rate of 2.5% fw/bw (feed weight/body weight) for two weeks. Fish in the control group received normal feed only.

Fish were challenged by immersion for 45 minutes in 10 L of water containing *E. ictaluri* S97-773. All fish from the same group were immersed in a single container. The concentration of *E. ictaluri* S97-773 was determined to be $4.5 \times 10^6$ CFU/ml. The challenge condition for the control group was the same as other treatments except that BHI medium was added instead of *E. ictaluri* culture. Mortalities were monitored over a 21-day period, and dead fish were dissected and the presence of *E. ictaluri* confirmed by microbiological examination of kidney and liver swabs on TSA. The identity of the recovered *E. ictaluri* was confirmed by biochemical analysis.

Fish were reared in a recirculating system during the acclimation period. Upon initiation of *Bacillus* feeding and during the challenge phase, a static system was incorporated with a 20-30 minutes water exchange daily. Sponge biofilters and daily removal of uneaten/waste materials were incorporated to control potential water quality problems. Water temperature was kept at 26±2° C. During the static phase, the central room heating system in conjunction with submersible aquarium water heaters was used to control the required water temperature, and a water heater system was used to control the temperature of the incoming water during water exchange.

Another challenge trial using channel catfish was conducted with a lower dose of *E. ictaluri* and flow-through conditions. In this challenge experiment, five *Bacillus* treatments (AP79, AP143, AP193L, and AB01) and one control each with four replicate aquaria were included. Each aquarium was stocked with 20 fingerling channel catfish (~12 g). A lower dose of *E. ictaluri* S97-773 ($8 \times 10^5$ CFU/ml) was used to challenge fish and starting immediately after challenge the aquaria were flushed for 5-8 hours a day. All other conditions in this challenge were the same as in the previous one. Mortalities were monitored over a 21-day period after challenge, and presence of *E. ictaluri* in the dead fish was confirmed as previously described.

An additional challenge trial was conducted to evaluate the protective effect of four *Bacillus* strains (AP79, AP193L, AP254L, and AB01) against *E. ictaluri* for striped catfish. Five treatments with four replicate tanks each were included in this study. Each tank was stocked with 18 striped catfish (~14 g). Striped catfish were administered feed amended with *Bacillus* spores (~$10^7$ CFU/g feed) and control feed for 2 weeks and the fish were transferred to 80 L tanks for a bath challenge with *E. ictaluri* NLF33. Fish were immersed for 30 min in static, aerated aquaria at a dose of ~$10^6$ CFU/mL to target about 70% mortality in the control group. The control and test diets were offered throughout the challenge phase. The recording of mortality and confirmation of *E. ictaluri* in dead fish were conducted as above.

Plasmid Analysis.

Plasmid DNA was extracted from *Bacillus* strains AP79, AP193L, and AB01, by alkaline lysis method (Birnboim and Doly 1979). *Bacillus subtilis* 1E17 containing plasmid pC194 was used as a positive control. The extracted DNA was analyzed by a Chef-DR II pulsed field electrophoresis system (Bio-Rad, Hercules, Calif.). Pulse time ranged from 1 to 15 seconds for 15 hours at 6 V/cm. The gel was stained with ethidium bromide and visualized using an AlphaImager HP gel documentation system (ProteinSimple, Santa Clara, Calif.).

Antibiotic Resistance Analysis.

The susceptibility of *Bacillus* strains AP79, AP193L, and AB01 to carbenicillin, ampicillin, spectinomycin, oxacillin, vancomycin, cephalothin, novobiocin, sulfadiazine, amikacin, erythromycin, neomycin, penicillin, chloramphenicol, sulfamethoxazole, norfloxacin, gentamicin and ciprofloxacin was determined by disc diffusion test following procedures outlined by National Committee for Clinical Laboratory Standards (CLSI 2012). A log-phase culture of each strain was diluted to a concentration of approximately $1 \times 10^8$ to $2 \times 10^8$ CFU/ml (McFarland standard 0.5). The inoculum was then seeded onto a Mueller-Hinton agar plate using a cotton swab. Antibiotic-impregnated discs (BD Biosciences) were placed on seeded plates, and the diameter of the zone of growth inhibition was measured after 18 h of incubation at 37° C. The experiments were repeated three times and the average diameter of inhibition zones was calculated.

Statistics.

Completely randomized design was used in this research. Data were presented as mean±standard error (SE). Challenge data were subjected to analysis of variance in SAS 9.2. Differences between means were tested by Tukey's range test and were considered significant when probability (P) values<0.05 were obtained.

Results

Characterization of *Bacillus* Isolates.

Each of the *Bacillus* strains isolated from soil or catfish intestine that exhibited inhibitory activity against both *E. ictaluri* and *A. hydrophila* was capable of endospore formation. Each pure *Bacillus* culture was ribotyped, indicating that most of the *Bacillus* strains were within the *B. subtilis* group (inclusive of *B. amyloliquefaciens*), with two strains of *B. pumilus* also within the collection. Since *B. subtilis* or *B. amyloliquefaciens* isolates cannot be conclusively differentiated based on biochemical or 16S rRNA gene sequence data, in some cases genome sequence data were available (i.e., for strains AP18, AP143, AP193L, and AP254L) and were used for phylogenetic classification. For each of these strains there was >80% identity to the most closely related *Bacillus* strain genome, providing unequivocal evidence of phylogenetic affiliation. Of the strains selected for genome sequencing, only strain AP193L was selected solely on the basis of its antagonism against aquaculture pathogens and efficacy in reducing mortality due to ESC. A full annotation of these genomes is beyond the scope of this study, but these genome sequences do provide an objective assessment of phylogeny and indicate putative biosynthetic pathways for antimicrobial synthesis that may be relevant to biological control of catfish pathogens (data not shown).

Antimicrobial Activity of *Bacillus* Strains.

The *Bacillus* strain AB01 isolated from the catfish intestine showed significant antimicrobial activity against *E. ictaluri*. From the collection of soil-derived *Bacillus* strains, 50 strains showed significant antagonism against *E. ictaluri*. All of the 50 *Bacillus* strains also showed inhibitory activity against *E. ictaluri* R-4383 and *E. ictaluri* Alg-08-200. A total of 21 *Bacillus* strains showed potent antibiotic activity against both *E. ictaluri* and *A. hydrophila* (e.g., FIG. 1). The 21 *Bacillus* strains selected were tested for their activity against multiple pathogens in aquaculture. All of the strains were antagonistic against multiple catfish pathogens, including Gram-negative and -positive bacteria, and the oomycete *Saprolegnia*. *Bacillus* strains AB01, AP193L, AP219, and AP301 showed antimicrobial activity against all of the tested pathogens (Table 1). Also, all of the five tested *Bacillus* strains (AP79, AP143, AP193L, AP254L, and AB01) showed significant antagonistic activity against *E. ictaluri* NLF33.

Survival and Persistence of *Bacillus* Strains in the Intestine of Channel Catfish.

Figure 4:
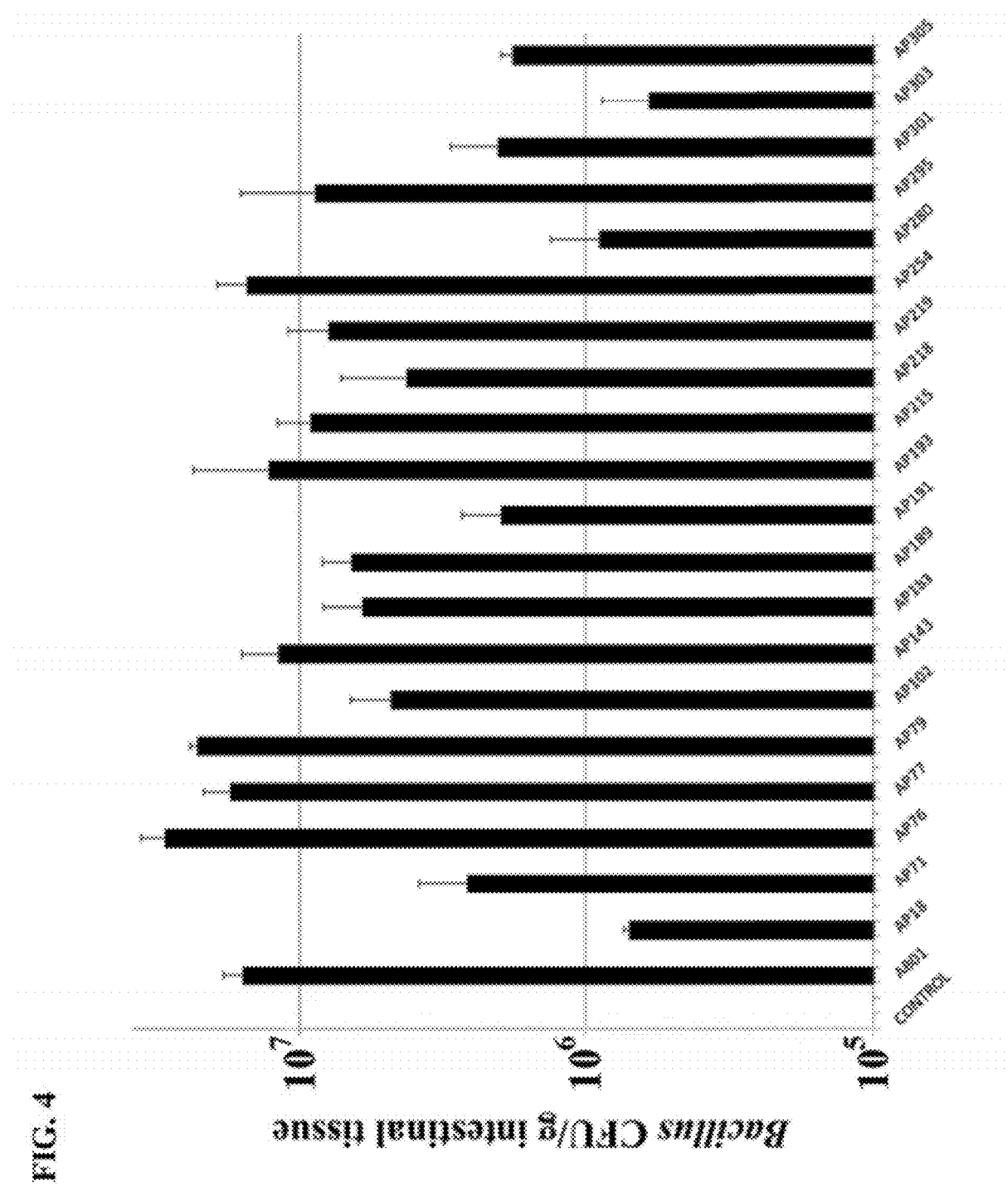
FIG. 4. illustrates the concentration of *Bacillus* strain CFUs/g in catfish intestine, after feeding with *Bacillus*-amended or non-amended feed (n=3 animals per *Bacillus* strain).

Administered bacteria were recovered from the intestine. Over $10^7$ CFU/g of introduced *Bacillus* was observed in the gut for strains AB01, AP76, AP77, AP79, AP143, and AP254L (FIG. 4). For strains AP18, AP280, and AP303, the counts of recovered bacteria were relatively low, and they were eliminated from further investigation. None of the 21 *Bacillus* strains were recovered from the control group. In all cases the 16S rRNA gene sequence determined from representative colonies matched the 16S rRNA gene sequence from the respective *Bacillus* strain that was added to catfish feed. For some of the *Bacillus* strains that were observed to have high CFU/g intestinal counts (e.g., strains AB01 and AP76), the only colonies observed at the $10^{-6}$ and $10^{-7}$ dilutions corresponded to the respective *Bacillus* colony morphology.

Challenge Study.

In the first challenge, the mean mortality of the control group was 98.0%. Treatment groups of *Bacillus* strains AP143 or AB01 showed significantly reduced mortality compared with the control (P<0.05), with 83.1%, 84.8%, and 79.6% mortality for these strains, respectively. And there is no significant difference among the two strains. The treatment groups of *Bacillus* strains AP79, AP193L, or AP254L (with mortality 89.0%, 95.0%, and 93.7%, respectively) did not show significant differences compared with the control (FIG. 5A, Table 2). For the second challenge, 41.3% of the fish died in the control group. The mortality in the treatment groups ranged from 35.0% to 46.3% with no significant differences observed between any of the treatment groups and the control (FIG. 5B, Table 2).

In the striped catfish challenge experiment, the treatment group fed strain AP79 spore-amended feed had the lowest (9.7%) cumulative mortality and was significantly different from the control (P<0.05). The treatment group fed strain AP193L-amended feed attained 30.6% mortality; however, it should be noted that most of the mortality was recorded in a single aquarium tank on day 4 of the challenge. Catfish fed with strains AP254L and AB01 had 54.2% and 56.9% mortality, respectively, while the control group had 70.8% mortality (FIG. 5C, Table 2).

Plasmid and Antibiotic Resistance Study.

An analysis of plasmid DNA content for selected *Bacillus* strains was conducted by PFGE, and we did not observe the presence of any plasmid within these four strains but the positive control did show the presence of plasmid pC194 (data not shown). Evaluation of antibiotic susceptibility determined that all four strains were susceptible to all of the tested antibiotics to varying degrees. They were all highly susceptible to carbenicillin, cephalothin, sulfamethoxazone and ciprofloxacin (>25 mm of diameter of inhibition zone). Ampicillin, penicillin, vancomycin, novobiocin, amikacin, erythromycin, neomycin, chloramphenicol, norfloxacin and gentamicin also inhibited their growth effectively (20-25 mm zone of inhibition), whereas spectinomycin, oxacillin, sulfadiazine showed moderate inhibition (15-20 mm inhibition zone). These four strains showed very similar antibiograms, with the variation of diameters of inhibition zone within the four strains lower than 10% of the average diameter for each of the antibiotics tested.

Discussion

The results of this study indicate that specific strains within the *Bacillus subtilis* group show promise for disease control in catfish aquaculture. In previous research, application of *Bacillus* cultures to pond water resulted in improved fish survival and yield (Queiroz and Boyd 1998). However, *Bacillus* cultures used in the latter study had not been evaluated for antagonism against *E. ictaluri* or other aquaculture pathogens. Furthermore, the ability of the *Bacillus* cultures from this commercial product to reduce the mortality or disease symptoms due to ESC was not evaluated and was complicated due to an infection of catfish by proliferative gill disease during the experimental period. This study is the first to select probiotic bacteria for control of ESC and other pathogens in catfish and to evaluate for their biocontrol efficacy via feed administration. *Bacillus* spp. were used in this research as they could be applied in spore form, thus facilitating easy storage and application, and many of the *Bacillus* strains had been previously studied for their ability to antagonize bacterial and/or fungal pathogens of plants (Kloepper et al. 2004).

Gatesoupe (1999) concluded that probiotics for aquaculture should be antagonistic to pathogens, colonize intestines, and increase resistance of the host to pathogens. Ideally probiotic bacteria should be selected by considering all three criteria. However, it is difficult to evaluate potential probiotic bacterial strains for the second and third criterion on a large number of candidate bacteria. Therefore, in vitro antimicrobial activity was the primary criteria by which a large number of strains were evaluated, with candidate bacterial strains that did not show antagonistic activity eliminated from further study. The primary objective of this research project was to identify bacterial strains that can be applied for the control of *E. ictaluri*, *A. hydrophila*, and other bacterial and oomycete pathogens of catfish. Since the bacterial pathogens *E. ictaluri* and *A. hydrophila* are responsible for the majority of the mortality observed currently in catfish aquaculture, the ability of a *Bacillus* strain to inhibit the growth of these two pathogens was of paramount importance and only the strains capable of inhibiting both pathogens were selected for testing in aquarium disease challenges.

The ability of a probiotic bacterial strain to colonize and survive within or on its host is also an important criterion for strain selection. However, in many cases the probiotic bacteria may not permanently colonize the gastrointestinal tract but instead achieve a sustained transient state (Robertson 2000; Irianto and Austin 2002). Even transient bacteria may be efficient at mediating biological control of disease if the cells are introduced artificially via food either continuously or semi-continuously (Gournier-Chateau et al. 1994; Gatesoupe 1999). High population levels of several *Bacillus* strains were recovered from catfish intestines three days post-feeding with *Bacillus*-spore amended feed. For *Bacillus* strains with high counts in the intestine, colonies with the same morphology as the applied *Bacillus* strain dominated the TSA plates, and the ribotype of the representative colonies confirmed their identity as the applied *Bacillus* strain. In a previous study of the persistence of an *E. ictaluri*-specific bacteriophage within the intestine of channel catfish, it was observed that 72 hours post-feeding the bacteriophage could not be detected within intestinal samples (Carrias 2011). This implies that any inert particle would be cleared from the catfish intestine by 72 hours post-feeding and that bacterial strains detected after this time frame would have some degree of intestinal persistence. Considering that bacterial population levels in the intestine should decline after cessation of feeding with the spore-containing diets, the maximal level of *Bacillus* strain CFU/g of intestinal tissue reached during the feeding regime may be higher. The bacterial population levels here ($10^6$-$10^7$ CFU/g for most of the strains) are in general agreement with previous studies involving fish (Jöborn et al. 1997; Gildberg and Mikkelsen 1998; Robertson et al. 2000; Irianto and Austin 2002). These results demonstrate that some of the *Bacillus* strains evaluated in this study can persist within the catfish gastrointestinal tract for at least three days. However, at this point the degree of persistence and ability to colonize the intestinal mucosa are unknown for each strain. A more detailed experiment evaluating the colonization and/or persistence of specific *Bacillus* strains within the catfish intestine will be conducted to help understand the biocontrol mechanism(s) of *Bacillus* strains and guide the duration and timing of *Bacillus* feeding. Future studies will also examine the impact of each *Bacillus* strain on the intestinal microbiota and the health and growth of the fish in the absence of aquaculture pathogens.

In one of the ESC challenge studies a very high mortality (98.0%) was observed in the control group, which may have affected the degree of protection that could be afforded by *Bacillus* strains. Ideally, an aquarium disease challenge would result in a mortality of 60%-70%, which more accurately simulates the natural development of ESC. The high mortality was probably a consequence of maintaining a static system during the challenge, wherein the *E. ictaluri* persisted in the tank for an extended period of time. Despite the higher mortality observed in this challenge, two *Bacillus* strains (AP143 and AB01) provided significant protection to channel catfish. It is important to note that the two challenges that showed protective effects for *Bacillus* strains were in a static system with 20-30 minutes of water exchange daily, while the challenge with no significant effect was conducted in a system flushed for 5-8 h every day after challenge. This suggests that a more pond-like environment wherein the probiotic is maintained within the water, and potentially the skin and gills of the fish, may be more conducive for effective biological control of disease. In addition, presumably at the lower doses of *E. ictaluri* that catfish are typically exposed to in an aquaculture pond the degree of biocontrol provided by *Bacillus* strains would be of an even greater magnitude.

The challenge study with striped catfish revealed reduced levels of mortality due to *E. ictaluri* for all of *Bacillus* strains, especially with the use of strain AP79 that reduced mortality to only 9.7% compared to the control level of 70.8% mortality. It is interesting that the relative biocontrol activity of tested *Bacillus* strains was different in the two catfish species. This could reflect a biologically meaningful difference in the interactions between *Bacillus* strains and their respective host. Also, there could be unique tripartite interactions between host, pathogen, and probiotic bacteria that could be influenced by environmental factors. Clearly more research is needed to understand the complex interplay between host, pathogen and probiotic *Bacillus* strains, and how to manipulate the environment to achieve the optimal biological control of disease. Further studies using an aquarium disease model with static conditions need to be conducted to optimize important parameters for challenge such as dosage and timing with the best performing *Bacillus* strains, with subsequent studies at a pond-scale to evaluate biological control efficacy within an aquaculture pond ecosystem.

One of the safety requirements for live bacteria directly consumed by humans is the absence of any acquired resistance to clinically important antibiotics (Sorokulova 2008). Although the *Bacillus* strains used in this research were not for direct consumption by humans, they might be consumed inadvertently, as their hosts were cultured for food. Thus, it is important to analyze antibiotic resistance in probiotic strains and to distinguish the natural resistance, which is one of the phenotypic characteristics of a species, and acquired (i.e., transferable) resistance, which is associated with occurrence of plasmids. Also, pathogenicity and enterotoxin production are closely associated with plasmids (Pannucci et al. 2002). None of the selected *Bacillus* strains carried any plasmids, and each of the strains was susceptible to a broad spectrum of antibiotics tested, which ensures their inability to conjugally transfer any plasmid that might confer antibiotic resistance.

Knowledge of the secondary metabolites expressed by each *Bacillus* strain may improve the rational selection of strains and strain "cocktails" to enhance biological control efficacy against aquaculture pathogens. *Bacillus* strains with similar antibiosis profiles against aquaculture and plant pathogens may be grouped together (Kloepper et al. 2004). The antimicrobial compound(s) produced by strains from different antibiosis groups should be different. Presumably the combination of strains from different antibiosis groups will provide even greater biocontrol of disease due to production of multiple antibiotic compounds acting by different mechanisms. Diffusible antimicrobial compounds were clearly involved in the in vitro antagonistic activity observed in soft agar overlay and in diffusion tests. The relative importance of secondary metabolites for in vivo biological control is unknown compared to enhancing fish immune competence and/or competitive exclusion mechanisms of pathogen antagonism. Future studies will investigate the relative contribution of specific antibiotic compounds to the biological control activity of some *Bacillus* strains.

In conclusion, a collection of *Bacillus* strains was identified that are antagonistic to the primary pathogens of catfish and are beneficial to both channel catfish and striped catfish when administered on feed for the control of ESC and BNP, respectively. These bacteria have potential application in aquaculture as a cost-effective alternative to the current use of antimicrobial compounds.

REFERENCES

Austin, B., Stuckey, L. F., Robertson, P., Effendi, L and Griffith, D. (1995) A probiotic strain of *Vibrio alginolyticus* effective in reducing diseases caused by *Aeromonas salmonicida, Vibrio anguillarum* and *Vibrio ordalii. J Fish Dis* 18, 93-96.

Austin, B. and Austin, D. A. (1999) *Bacterial Fish Pathogens, Disease in Farmed and Wild Fish*, 3$^{rd}$ (revised) edn. Godalming: Springer-Praxis.

Birnboim, H. C. and Doly, J (1979) A rapid alkaline extraction procedure for screening recombinant plasmid DNA. *Nucleic Acids Res* 7, 1513-1523.

Brunt, J. and Austin, B. (2005) Use of a probiotic to control lactococcosis and streptococcosis in rainbow trout, *Oncorhynchus mykiss* (Walbaum). *J Fish Dis* 28, 693-701.

Carrias, A. A. (2011) Evaluation of Biological Agents for Controlling Enteric Septicemia of Catfish. Thesis. Auburn, Ala.: Department of Fisheries and Applied Aquacultures, Auburn University.

Chang, C. I. and Liu, W. Y. (2002) An evaluation of two probiotic bacterial strains, *Enterococcus faecium* SF68 and *Bacillus toyoi*, for reducing edwardsiellosis in cultured European eel, *Anguilla anguilla* L. *J Fish Dis* 25, 311-315.

Cipriano, R. C., Bullock, G. L., and Pyle, S. W. (1984) *Aeromonas hydrophila* and motile aeromonad septicemia of fish. U.S. Fish and Wildlife Service, Fish Disease Leaflet 68:23.

Delbos, B. C., Weirich, C. R., Fernandez, D., and Thune, R. Evaluation of a live attenuated vaccine for the control of enteric septicemia of catfish under simulated production conditions. Aquaculture 2001: Book of Abstracts, 177. 2001.

DePaola, A., Peeler, J. T. and Rodrick, G. E. (1995) Oxytetracycline-medicated feed on antibiotic resistance of gram-negative bacteria in Catfish Ponds. *Appl Environ Microbiol* 61, 2335-2340.

De Silva, S. S., Ingram, B. A., Nguyen, P. T., Bui, T. M., Gooley, G. J. and Turchini, G. M. (2010) Estimation of nitrogen and phosphorus in effluent from the striped catfish farming sector in the Mekong Delta, Vietnam. *Ambio* 39, 504-514.

Enebak, S. A., Wei, G., and Kloepper, J. W. (1998) Effects of plant growth-promoting rhizobacteria on loblolly and slash pine seedlings. *Forest Science*, 44:139-144.

Farmer, B. (2004) Improved methods for the isolation and characterization of *Flavobacterium columnare*. Thesis. Baton Rouge, La.: Department of Pathobiological Sciences, Louisiana State University.

Ford, L. A., and Thune, R. L. (1991) S-layer positive motile aeromonads isolated from channel catfish, *Journal of Wildlife Diseases* 27:557-561.

Fuller, R. and Turvey, A. (1971) Bacteria associated with the intestinal wall of the fowl (*Gallus domesticus*). *J Appl Bacteriol* 34, 617-622.

Fuller, R. (1987) A review: probiotics in man and animals. *J Appl Bacteriol* 66, 365-378.

Fuller, R. (1997) *Probiotics 2, Applications and Practical Aspects*. London: Chapman & Hall.

Gatesoupe, F. J. (1999) The use of probiotics in aquaculture. *Aquaculture* 180, 147-165.

Gaunt, P., Endris, R., Khoo, L., Leard, A. T., Jack, S., Santucci, T., Katz, T., Radecki, S. V., and Simmons, R. Preliminary Assessment of the Tolerance and Efficacy of Florfenicol against *Edwardsiella ictaluri* Administered in Feed to Channel Catfish. Journal of Aquatic Animal Health 15(3), 239-247. 2003.

Gaunt, P. S., Endris, R. G., Khoo, L. H., Howard, R., McGinnis, A. L., Santucci, T. D., and Katz, T. Determination of Dose Rate of Florfenicol in Feed for Control of Mortality in Channel Catfish *Ictalurus punctatus* (Rafinesque) Infected with *Edwardsiella ictaluri*, Etiological Agent of Enteric Septicemia. Journal of the World Aquaculture Society 35(2), 257-267. 2004.

Gerald, D. A. and Jane, E. B. (1966) Effect of the normal microbial flora on the resistance of the small intestine to infection. *J Bacteriol* 92, 1604-1608.

Gildberg, A. and Mikkelsen, H. (1998) Effects of supplementing the feed to Atlantic cod (*Gadus morhua*) fry with lactic acid bacteria and immuno-stimulating peptides during a challenge trial with *Vibrio anguillarum. Aquaculture* 167, 103-113.

Gournier-Chateau, N., Larpent, J. P., Castellanos, I. and Larpent, J. L. (1994) *Les Probiotiques en Alimentation Animale et Humaine* pp. 192. Paris: Technique et Documentation Lavoisier.

Harikrishnan, R., Nisha Rani, M. and Balasundaram, C. (2003) Hematological and biochemical parameters in common carp, *Cyprinus carpio*, following herbal treatment for *Aeromonas hydrophila* infection. *Aquaculture* 221, 41-50.

Harlander, S. K. (2002) The Evolution of Modern Agriculture and Its Future with Biotechnology. *Journal of the American College of Nutrition*, 21:161 S-165S.

Hawke, J. P., 1979: A bacterium associated with disease of pond cultured channel catfish, *Ictalurus punctatus*. Journal of the Fisheries research Board of Canada 36, 1508-1512.

Hawke, J. P. and Khoo, L. H. (2004) Infectious diseases. In *Biology and Culture of Channel Catfish* ed. Tucker, C. S. and Hargreaves, J. A. pp. 387-443. Amsterdam, The Netherlands: Elsevier.

Hawke, J. P., McWhorter, A. C., Steigerwalt, A. G., and Brenner, D. J., 1981: *Edwardsiella ictaluri* sp. nov., the causative agent of enteric septicemia of catfish. International Journal of Systemic Microbiology 31, 396-400.

Hossain, M. J., Rahman, K. H., Terhune. J. S., and Liles, M. R. An outer membrane porin protein modulates phage susceptibility of *Edwardsiella ictaluri*. Microbiology. 2012 February; 158(pt2):474-87. Epub 2011 Dec. 1.

Irianto, A. and Austin, B. (2002) Use of probiotics to control furunculosis in rainbow trout, *Oncorhynchus mykiss* (Walbaum). *J Fish Dis* 25, 333-342.

Jack, R. W., Wan, J., Gordon, J., Harmark, K., Davidson, B. E., Hillier, A. J., Wettenhall, R. E., Hickey, M. W. and Coventry, M. J. (1996) Characterization of the chemical and antimicrobial properties of piscicolin 126, a bacteriocin produced by *Carnobacterium piscicola* JG126. *Appl Environ Microbiol* 62, 2897-2903.

JÖborn, A., Olsson, J. C., Westerdah, M. A., Conway, P. L. and Kjelleberg, S. (1997) Colonization in the fish intestinal tract and production of inhibitory substances in intestinal mucus and faecal extracts by *Carnobacterium* sp. strain K1. *J Fish Dis* 20, 383-392.

Johnson, M. R. (1991) Bacterial resistance to antibiotics: a growing problem in the channel catfish industry. In: *Proceedings of Louisiana Aquaculture Conference* ed. Reigh, R. C., pp. 22-23. Louisiana State University Agricultural Center, Baton Rouge, La.

Kenney, D. S. and Couch, T. L. (1981) Mass production of biological agents for plant disease, weed and insect control. In: *Biological Control in Crop Production BARC Symposium No. 5* ed. Papavizas, G. C., pp. 143-150. Totowa, N.J.: Allenheld and Osmum.

Khoo, L. Antibiotic resistance in the channel catfish industry. Aquaculture 2001: Book of Abstracts, 329. 2001.

Klesius, P. H. 1992. Carrier state of channel catfish infected with *Edwardsiella ictaluri*. Journal of Aquatic Animal Health 4(3), 227-230.

Kloepper, J. W., Reddy, M. S., Kenney, D. S., Vavrina, C., Kokalis-Burelle, N., and Martinez-Ochoa, N. (2004) Theory and applications of rhizobacteria for transplant production and yield enhancement. Proc. XXVI IHC—Transplant Production and Stand Establishment. Eds. S. Nicola, J. Nowak and C. S. Vavrina. Acta Hort. 631:217-229.

Kloepper, J. W., Ryu, C.-M., Zhang, S. 2004. Induced systemic resistance and promotion of plant growth by *Bacillus* spp. *Phytopathology,* 94:1259-1266.

Kokalis-Burelle, N., Vavrina, C. S., Reddy, M. S., and Kloepper, J. W. (2003) Amendment of muskmelon transplant media with plant growth-promoting rhizobacteria: effects on seedling quality, disease, and nematode resistance. *Hortechnology* 13:476-482.

Lategan, M. J., Torpy, F. R. and Gibson, L. F. (2004) Control of saprolegniosis in the eel *Anguilla australis* Richardson, by *Aeromonas media* strain A199. *Aquaculture* 240, 19-27.

Lewis, W. J., van Lenteren, J. C., Sharad, C., Phatak, C., and Tumlinson III, J. H. (1997). A total system approach to sustainable pest management. *Proceedings of the National Academy of Science USA,* 94:12243-12248.

Lim, C. and Klesius, P. H. Influence of Feed Deprivation on Hematology, Macrophage Chemotaxis, and Resistance to *Edwardsiella ictaluri* Challenge of Channel Catfish. Journal of Aquatic Animal Health 15(1), 13-20. 2003.

National Committee for Clinical Laboratory Standards (2012) *Performance Standards for Antimicrobial Disk Susceptibility Test*; Approved Standard-Ninth Edition. Wayne, Pa.: Clinical and Laboratory Standards Institute.

Pannucci, J., Okinaka, R. T., Sabin, R. and Kuske, C. R. (2002) *Bacillus anthracis* pXO1 plasmid sequence conservation among closely related bacterial species. *J Bacteriol* 184, 134-141.

Phan, L. T., Bui, T. M., Nguyen, T. T. T., Gooley, G. J., Ingram, B. A., Nguyen, H. V., Nguyen, P. T. and De Silva, S. S. (2009) Current status of farming practices of striped catfish, *Pangasianodon hypophthalmus* in the Mekong Delta, Vietnam. *Aquaculture* 296, 227-236, Phuong, N. T. and Oanh, D. T. H. (2009) Striped catfish (*Pangasianodon hypophthalmus*) aquaculture in Viet Nam: an unprecedented development within a decade. In: *Success Stories in Asian Aquaculture* ed. De Silva, S. S., Davy, F. B., pp. 133-149. Dordrecht, Bangkok and Ottawa: Springer, NACA and IDRC.

Plumb, J. A., 1999: *Edwardsiella septicaemias,* In: Woo, P. T. K., and Bruno, D. W. [Eds.] Fish Diseases and disorders, Vol. 3, pp 479-521.

Plumb, J. A., Sheifinger, C. C., Shryock, T. R. and Goldsby, T. (1995) Susceptibility of six bacterial pathogens of channel catfish to six antibiotics. *J Aquat Anim Health* 7, 211-217.

Pridgeon, J. W., Klesius, P. H., Mu, X. and Song, L. (2011) An in vitro screening method to evaluate chemicals as potential chemotherapeutants to control *Aeromonas hydrophila* infection in channel catfish. *J Appl Microbiol* 111, 114-124.

Queiroz, J. and Boyd, C. E. (1998) Effects of a Bacterial Inoculum in Channel Catfish Ponds. *J World Aquacult Soc* 29, 67-73.

Rengpipat, S., Phianphak, W., Piyatiratitivorakul, S. and Menasveta, P. (1998) Effects of a probiotic bacterium on black tiger shrimp *Penaeus monodon* survival and growth. *Aquaculture* 167, 301-313.

Rhaman, M. H., Suzuki, S. and Kawai, K. (2001) The effect of temperature on *Aeromonas hydrophila* infection in goldfish, *Carassius auratus. J Appl Ichthyol* 17, 282-285.

Robertson, P. A. W., O'Dowd, C., Burrells, C., Williams, P. and Austin, B. (2000) Use of *Carnobacterium* sp. as a probiotic for Atlantic salmon (*Salmo salar* L.) and rainbow trout (*Oncorhynchus mykiss,* Walbaum). *Aquaculture* 185, 235-243.

Roach, S. and Tannock, G. W. (1980) Indigenous bacteria that influence the number of *Salmonella typhimurium* in the spleen of intravenously challenged mice. *Can J Microbiol* 26, 408-411.

Sanchis, V., and Bourguet, D. (2008) *Bacillus thuringiensis*: applications in agriculture and insect resistance management. A review. *Agronomy for Sustainable Development,* 28:11-20.

Serageldin, I. (1999) Biotechnology and food security in the 21st century. *Science,* 285:387-389.

Shoemaker, C. A., Klesius, P. H., and Bricker, J. M., 1999: Efficacy of a modified live *Edwardsiella ictaluri* vaccine in channel catfish as young as seven days post hatch. Aquaculture 176, 189-193.

Smoragiewicz, W., Bielecka, M., Babuchowski, A., Boutard, A. and Dubeau, H. (1993) Les probiotiques. *Can J Microbiol* 39, 1089-1095.

Sorokulova, I (2008) Preclinical testing in the development of probiotics: a regulatory perspective with *Bacillus* strains as an example. *Clin Infect Dis* 46, SS92-95.

Sugita, H., Miyajima, C. and Deguchi, Y. (1990) The vitamin B12-producing ability of intestinal bacteria isolated from tilapia and channel catfish. *Nippon Suisan Gakkaishi* 56, 701.

Tang, L., Shah, S., Chung, L., Carney, J., Katz, L., Khosla, C., and Julien, B. (2000) Cloning and heterologous expression of the epothilone gene cluster. Science 287:640-642.

USDA. Part I: Reference of Fingerling Catfish Health and Production Practices in the United States. 2003a. Fort Collins, Colo. #N406.1103, USDA:APHIS:VS:CEAH, National Animal Health Monitoring System.

USDA. Part II: Reference of Foodsize Catfish Health and Production Practices in the United States. 2003b. Fort Collins, Colo. #N407.1103, USDA:APHIS:VS:CEAH, National Animal Health Monitoring System.

U.S. Published Application No. 20100092431, published Apr. 15, 2010; Inventor(s): Liles, M. R., Walakira, J., Carrias, A., and Terhune, J.

Wagner, B. A., Wise, D. J., Khoo, L. H. and Terhune, J. S. (2002) The epidemiology of bacterial diseases in food-size channel catfish. *J Aquat Anim Health* 14, 263-272.

Walakira, J., Carrias, A., Hossain, M., Jones, E., Terhune, J. S., and Liles, M. R. (2008) Identification and characterization of bacteriophages specific to the catfish pathogen *Edwardsiella ictaluri*. *Journal of Applied Microbiology*, 105(6):2133-2142.

Weisburg, W. G., Barns, S. M., Pelletier, D. A. and Lane, D. J. (1991) 16S Ribosomal DNA Amplification for Phylogenetic Study. *J Bacteriol* 173, 697-703.

Welch, T. (2008) IncA/C Plasmid-Mediated Florfenicol Resistance in the Catfish Pathogen *Edwardsiella ictaluri*. Antimicrobial Agents and Chemotherapy, 53:845-846.

Wilson, A. C., M. Perego, and J. A. Hoch. (2007) New transposon delivery plasmids for insertional mutagenesis in *Bacillus anthracis*. J. Microbiol. Methods 71:332-335.

Wise, D. J., Camus, A. C., Schwedler, T. E., and Terhune, J. S., 2004: Health Management. In: C. S. Tucker and J. A. Hargreaves (eds.), Biology and Culture of Channel Catfish, Amsterdam, The Netherlands.

Wise, D. J. and Johnson, M. J., 1998: Effect of feeding frequency and Romet-medicated feed on survival, antibody response, and weight gain of fingerling channel catfish *Ictalurus punctatus* after natural exposure to *Edwardsiella ictaluri*. Journal of the World Aquaculture Society 29: 169-175.

Wise, D. J., Klesius, P. H., Shoemaker, C. A., and Wolters, W. R., 2000: Vaccination of mixed and full-sib families of channel catfish *Ictalurus punctatus* after natural exposure to *Edwardsiella ictaluri*. Journal of the World Aquaculture Society 31: 206-212.

Wise, D. J. and Terhune, J. S., 2001: The relationship between vaccine dose and efficacy in channel catfish *Ictalurus punctatus* vaccinated as fry with a live attenuated strain of *Edwardsiella ictaluri* (RE-33). Journal of the World Aquaculture Society 32: 177-183.

Zehnder, G. W., Murphy, J. F., Sikora, E. J. and Kloepper, J. W. (2001) Application of rhizobacteria for induced resistance. *European Journal of Plant Pathology*. 107:39-50.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

TABLE 1

Antimicrobial activity of 22 *Bacillus* strains against pathogens.

| Phylogeny | Strain | Aeromonas hydrophila | Edwardsiella ictaluri | Edwardsiella tarda | Flavobacterium columnare | Saprolegnia ferax | Streptococcus iniae | Yersinia ruckeri |
|---|---|---|---|---|---|---|---|---|
| *B. subtilis* group | AB01 | + | + | + | +++ | + | ++ | ++ |
| *B. pumilus*‡ | AP18 | + | + | − | − | + | + | − |
| *B. subtilis* group | AP71 | + | ++ | + | − | − | ++ | + |
| *B. cereus* | AP76 | + | ++ | ++ | − | + | ++ | ++ |
| *B. subtilis* group | AP77 | + | +++ | ++ | − | + | + | ++ |
| *B. subtilis* group, *B. amyloliquefaciens*‡ | AP79 | ++ | ++ | + | − | − | ++ | ++ |
| *B. subtilis* group | AP102 | + | ++ | ++ | ++ | + | − | ++ |
| *B. subtilis* group, *B. amyloliquefaciens*‡ | AP143 | ++ | ++ | ++ | − | + | + | ++ |
| *B. subtilis* group | AP183 | + | ++ | ++ | − | − | ++ | + |
| *B. subtilis* group | AP189 | ++ | +++ | ++ | − | − | ++ | + |
| *B. methylotrophicus* | AP191 | ++ | +++ | + | + | + | ++ | − |
| *B. subtilis* group, *B. amyloliquefaciens*‡ | AP193L | ++ | ++ | ++ | ++ | + | + | − |
| *B. subtilis* group | AP215 | + | +++ | + | − | + | + | ++ |
| *B. subtilis* group | AP218 | + | ++ | + | − | + | + | + |
| *B. subtilis* group | AP219 | ++ | ++ | + | + | + | ++ | + |
| *B. subtilis* group, *B. amyloliquefaciens*‡ | AP254L | + | ++ | + | ++ | − | − | − |
| *B. pumilus* | AP280 | + | ++ | + | − | + | + | + |
| *B. subtilis* group | AP295 | + | ++ | + | − | + | + | ++ |
| *B. subtilis* group | AP301 | + | ++ | + | +++ | + | ++ | + |
| *B. subtilis* group | AP303 | ++ | ++ | ++ | − | + | + | ++ |
| *B. subtilis* group | AP305 | ++ | ++ | ++ | − | − | + | ++ |

(+) Zone of inhibition up to 5 mm;
(++) Zone of inhibition from 5 mm to 1 cm;
(+++) Zone of inhibition greater than 1 cm.
(−) No observable zone of inhibition.
‡Phylogenetic affiliation inferred from a comparison of these *Bacillus* strain genome sequences with previously sequenced *Bacillus* genomes.

TABLE 2

Mortality (%) (±SE) of groups of fish that received feed amended with different *Bacillus* strains or control feed and were challenged with *E. ictaluri* (n = 4).

| Treatment | Channel catfish challenge (FIG. 5.A) | Channel catfish challenge (FIG. 5.B) | Striped catfish challenge (FIG. 5.C) |
|---|---|---|---|
| Control | 98.0 ± 1.16[a] | 41.3 ± 5.91[a] | 70.8 ± 7.31[a] |
| AB01 | 84.8 ± 1.95[bc] | 37.5 ± 9.46[a] | 56.9 ± 6.56[ab] |
| AP143 | 83.1 ± 2.88[bc] | 43.3 ± 14.81[a] | Not determined |
| AP193L | 95.0 ± 3.00[ab] | 35.0 ± 5.40[a] | 30.6 ± 23.73[ab] |
| AP254L | 93.7 ± 2.79[ab] | Not determined | 54.2 ± 11.43[ab] |
| AP79 | 89.0 ± 2.74[abc] | 46.3 ± 5.15[a] | 9.7 ± 6.56[b] |

Means in the same column sharing a common superscript letter were not significantly different (P > 0.05) as determined by Tukey's test.

The invention claimed is:

1. A pelleted feed composition for aquatic animals, wherein the feed is provided with a coating and the feed composition comprises a spore-forming strain of *Bacillus* having a 16S rDNA sequence comprising SEQ ID NO: 1, SEQ ID NO: 2, or SEQ ID NO: 3, or comprising a 16S rDNA sequence having at least 99% sequence identity to SEQ ID NO: 1, SEQ ID NO: 2, or SEQ ID NO: 3, wherein the spore-forming strain of the *Bacillus* is present at a concentration of at least $10^4$ CFU/g of the feed composition.

2. The feed composition of claim 1, wherein the spore-forming strain of the *Bacillus* is a *Bacillus* species having a 16S rDNA comprising SEQ ID NO: 1, SEQ ID NO: 2, or SEQ ID NO: 3.

3. The feed composition of claim 1, wherein the spore-forming strain of the *Bacillus* is susceptible to one or more antibiotics selected from the group consisting of carbenicillin, ampicillin, spectinomycin, oxacillin, vancomycin, cephalothin, novobiocin, sulfadiazine, amikacin, erythromycin, neomycin, penicillin, chloramphenicol, sulfamethoxazole, norfloxacin, gentamicin and ciprofloxacin.

4. The feed composition of claim 1, wherein the feed composition is a feed composition for farmed fish.

5. The feed composition of claim 1, wherein the spore-forming strain of the *Bacillus* is the single strain of *Bacillus* present in the feed composition.

6. The feed composition of claim 1, wherein the composition comprises a mixture of spore-forming strains of *Bacillus*.

7. The feed composition of claim 1, wherein the spore-forming strain of the *Bacillus* is selected from the group consisting of *Bacillus* strains deposited under the accession numbers NRRL B-50745, NRRL B-50741, NRRL B-50742, NRRL B-50743, and NRRL B-50744.

8. A pelleted feed composition for aquatic animals, wherein the feed is provided with a coating and the feed composition comprises a spore-forming strain of *Bacillus*, wherein the spore-forming strain of *Bacillus* is a *Bacillus* species having a 16S rDNA comprising SEQ ID NO: 1, SEQ ID NO: 2, or SEQ ID NO: 3, and the spore-forming strain of the *Bacillus* is present at a concentration of at least $10^4$ CFU/g of the feed composition.

9. The feed composition of claim 8, wherein the spore-forming strain of the *Bacillus* inhibits the growth of one or more bacteria selected from the group consisting of *Aeromonas hydrophila*, *Flavobacterium columnare*, *Edwardsiella ictaluri*, *Edwardsiella tarda*, *Streptococcus iniae*, and *Yersinia ruckeri*.

10. A pelleted feed composition for aquatic animals, wherein the feed is provided with a coating and the feed composition comprises a spore-forming strain of *Bacillus* selected from the group consisting of *Bacillus* strains deposited under the accession numbers NRRL B-50745, NRRL B-50741, NRRL B-50742, NRRL B-50743, and NRRL B-50744, and wherein the spore-forming strain of the *Bacillus* is present at a concentration of at least $10^4$ CFU/g of the feed composition.

* * * * *